US012636398B2

(12) United States Patent
Mou et al.

(10) Patent No.: US 12,636,398 B2
(45) Date of Patent: May 26, 2026

(54) PURIFICATION DEVICE OF EXERCISE ENVIRONMENT

(71) Applicant: Microjet Technology Co., Ltd., Hsinchu (TW)

(72) Inventors: Hao-Jan Mou, Hsinchu (TW);
Ching-Sung Lin, Hsinchu (TW);
Chin-Chuan Wu, Hsinchu (TW);
Chi-Feng Huang, Hsinchu (TW);
Yung-Lung Han, Hsinchu (TW);
Chang-Yen Tsai, Hsinchu (TW);
Chin-Wen Hsieh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 1368 days.

(21) Appl. No.: 17/360,103

(22) Filed: Jun. 28, 2021

(65) Prior Publication Data

US 2022/0001067 A1 Jan. 6, 2022

(30) Foreign Application Priority Data

Jul. 3, 2020 (TW) ................................ 109122667

(51) Int. Cl.
*A61L 9/20* (2006.01)
*A61L 9/14* (2006.01)
*A61L 9/22* (2006.01)
(52) U.S. Cl.
CPC .................. *A61L 9/145* (2013.01); *A61L 9/22* (2013.01); *A61L 2209/111* (2013.01);
(Continued)

(58) Field of Classification Search
CPC ........................................................ A61L 9/20
See application file for complete search history.

(56) References Cited

U.S. PATENT DOCUMENTS 6,494,940 B1 * 12/2002 Hak ...................... B01D 46/10
96/417
9,759,438 B2 9/2017 Cur et al.
(Continued)

FOREIGN PATENT DOCUMENTS

CN 209188372 U 8/2019
CN 209280665 U 8/2019
(Continued)

*Primary Examiner* — Donald R Spamer
(74) *Attorney, Agent, or Firm* — Birch, Stewart, Kolasch & Birch, LLP

(57) ABSTRACT

A purification device of exercise environment is provided and includes a main body, a purification unit, a gas guider and a gas detection module. The main body has at least one gas inlet and at least one gas outlet. The purification unit, the gas guider and the gas detection module are disposed in the main body. The purification unit filters a gas in an exercise environment introduced through the at least one gas inlet. The gas guider operates continuously to transport the gas in the exercise environment to be introduced through the at least one gas inlet and to flow through the purification unit. The gas detection module detects a gas information and a particulate cleanliness of the air in the exercise environment, and the particulate cleanliness of the gas in the breathing region around the nose of the exerciser reaches $0\text{~}20\ \mu g/m^3$ accordingly.

20 Claims, 31 Drawing Sheets

(52) U.S. Cl.
CPC ....... *A61L 2209/14* (2013.01); *A61L 2209/21*
(2013.01); *A61L 2209/22* (2013.01)

(56) References Cited

U.S. PATENT DOCUMENTS

| | | | | |
|---|---|---|---|---|
| 2008/0031783 A1* | 2/2008 | Briggs | ................. | B01D 53/885 |
| | | | | 442/43 |
| 2016/0023151 A1* | 1/2016 | Swenerton | ......... | B01D 46/0005 |
| | | | | 55/467 |
| 2017/0080373 A1* | 3/2017 | Engelhard | ............ | B01D 46/448 |
| 2017/0209719 A1* | 7/2017 | Tang | ................... | A62B 23/025 |
| 2017/0218940 A1* | 8/2017 | Chen | ....................... | F04B 53/10 |
| 2019/0056292 A1 | 2/2019 | Mou et al. | | |
| 2019/0178775 A1* | 6/2019 | Feng | .................... | F04B 45/047 |

FOREIGN PATENT DOCUMENTS

| | | |
|---|---|---|
| CN | 110501454 A | 11/2019 |
| CN | 110732206 A | 1/2020 |
| CN | 106642323 B | 5/2020 |
| TW | I577944 B | 4/2017 |
| TW | I801915 B | 10/2017 |
| TW | M592495 U | 3/2020 |
| TW | 202014889 A | 4/2020 |

* cited by examiner

4b

PURIFICATION DEVICE OF EXERCISE ENVIRONMENT

FIELD OF THE INVENTION

The present disclosure relates to a purification device, and more particularly to a purification device applied in an exercise environment.

BACKGROUND OF THE INVENTION

The ventilation volume of human is about 10,000 liters per day without exercise, and it would become 10-20 times the normal amount when we exercise vigorously, especially during aerobic exercising. Exercising outdoors in the poor air condition, the dirt we sucked into our body is beyond imagination and would cause a lot of burden on the cardiovascular system. Even young people with normal cardiovascular systems might suddenly appear some problems at this time. This would be harmful to their health or even their life accordingly.

As mentioned above, recently, people pay more and more attention to the quality of the air around their daily lives. For example, carbon monoxide, carbon dioxide, volatile organic compounds (VOC), PM2.5, nitric oxide, sulfur monoxide and even the suspended particles contained in the air that expose in the environment might be harmful to the human health, and even endanger our life seriously. Therefore, the quality of environmental air has attracted the attention in various countries. Right now, how to monitor the air quality and avoid breathing in a dirty air and staying away from the environment with bad air quality is an issue of concern.

Using a gas sensor to monitor the air quality in an environment and confirm the air quality is feasible. Furthermore, if the gas sensor is able to provide the monitoring information for the people in this environment in real time and warn the people to take preventive measures or escape from this environment when a bad air quality is sensed, it would be helpful for people to avoid the negative impact and damage result from exposure in the bad air quality environment. Consequently, utilizing the gas sensor to monitor the environment is a great application in the life science.

Moreover, we should especially pay more attention to the air quality in the exercise environment. Therefore, providing a purification solution for purifying and improving the air quality, preventing people from breathing harmful gases in the indoor or outdoor exercise environment, and monitoring the air quality in real time anytime and anywhere is a major problem to be developed in the present disclosure.

SUMMARY OF THE INVENTION

An object of the present disclosure is to provide a purification device for exercise environment. A gas detection module is utilized to monitor the air quality of the exercise environment around the exerciser at any time, and a purification unit is utilized to provide a solution for purifying and improving the air quality. Through the combination of the gas detection module, the purification unit and the gas guider, a filtered gas amount of over 60 L/min is discharged out, and a directional filtered gas flow is formed and provided to a breathing region around the nose of the exerciser. Further, the particulate cleanliness of the gas in the breathing region reaches 0~20 $\mu g/m^3$. Alternatively, by the gas guider, the filtered gas flow with a clean air delivery rate of over 500 $m^3/hr$ is discharge out and provided to the breathing region around the nose of the exerciser. By this way, the exerciser can be prevented from breathing harmful gas in the indoor and/or outdoor exercise environment and obtain the real-time information as warning to notice the exerciser in the exercise environment c to take preventive measures immediately.

In accordance with an aspect of the present disclosure, a purification device of exercise environment including a main body is provided. The main body has at least one gas inlet and at least one gas outlet. The main body includes a purification unit, a gas guider and a gas detection module disposed therein. The purification unit filters a gas in an exercise environment introduced through the at least one gas inlet. The gas guider operates continuously to transport and introduce the gas in the exercise environment through the at least one gas inlet, flow through the purification unit, and provide to a breathing region around the nose of an exerciser. The gas detection module detects a gas information and a particulate cleanliness in the exercise environment, to allow the particulate cleanliness of the gas in the breathing region around the nose of the exerciser to reach 0~20 $\mu g/m^3$ accordingly.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
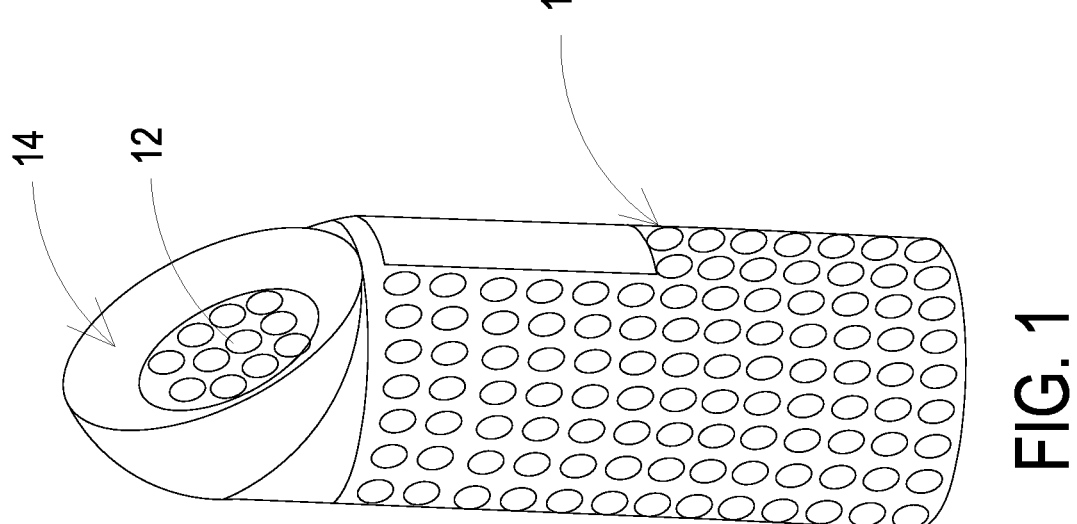
FIG. 1 is a schematic perspective view illustrating a purification device of exercise environment according to an embodiment of the present disclosure.
Figure 2A:
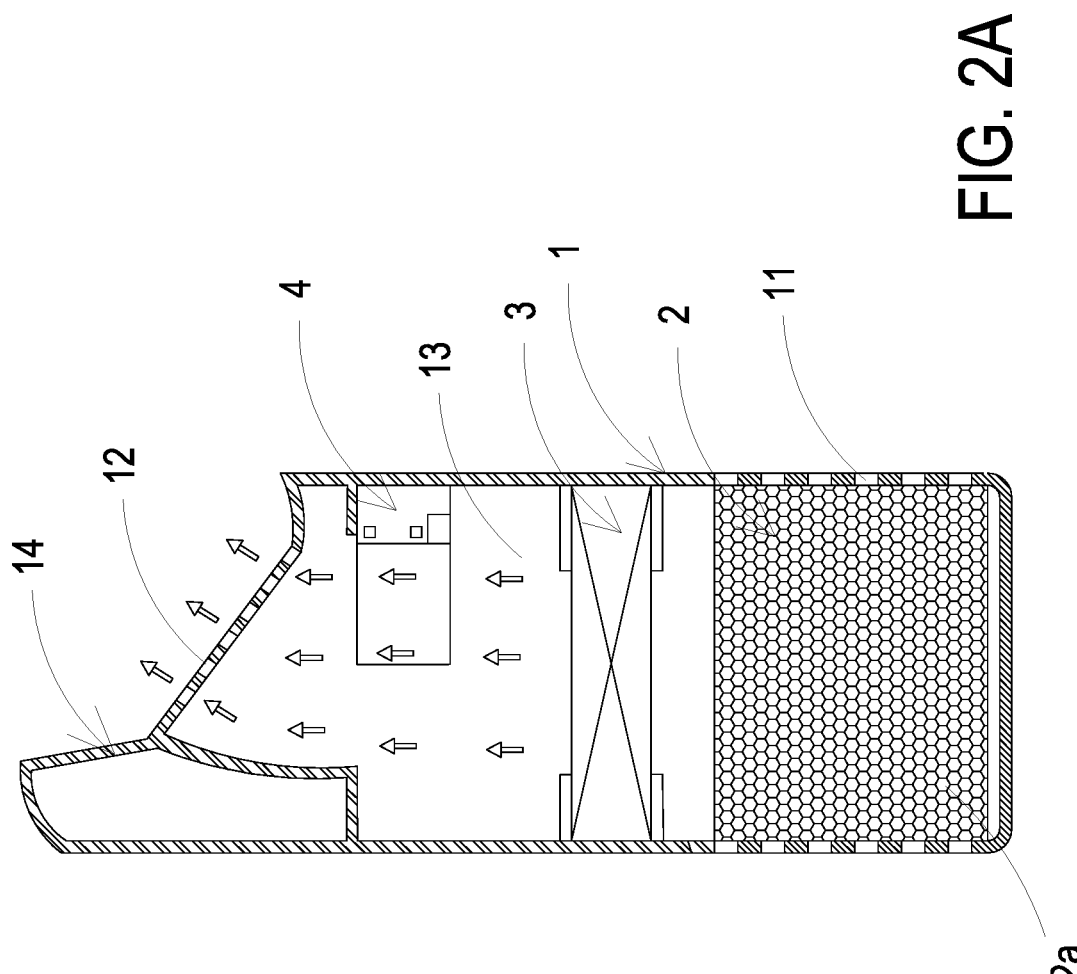
FIG. 2A is a cross-section view showing a filter screen of a purification unit of the purification device of exercise environment of the present disclosure.

Please refer to FIGS. 1 and 2A. The present disclosure provides a purification device of exercise environment including a main body 1, a purification unit 2, a gas guider 3 and a gas detection module 4. The main body 1 has at least one gas inlet 11 and at least one gas outlet 12. The gas in an exercise environment is introduced through the at least one gas inlet 11 and then filtered by the purification unit 2. The gas guider 3 operates continuously to transport the gas in the exercise environment to the purification unit 2 through the at least one gas inlet 11. Moreover, the gas detection module 4 is utilized to detect a gas information and a particulate cleanliness in the exercise environment. In the embodiment, the main body 1 is a directional gas-guiding device, and a directional guiding element 14 is disposed on the at least one gas outlet 12 of the main body 1. The ventilation of filtered gas above 60 L/min is discharged out through the at least one gas outlet 12 by the gas guider 3, and result in a directional filtered gas flow provided to a breathing region around the nose of the exerciser, and the particulate cleanliness of the gas in the breathing region can reach 0~20 μg/m³. Alternatively, in another embodiment, the main body 1 is a non-directional gas-guiding device. Namely, an open-type gas outlet is disposed on the gas outlet 12 of the main body 1 instead of a directional guiding element 14. The filtered gas flow with a clean air delivery rate of over 500 m³/hr is discharged out through the at least one gas outlet 12 by the gas guider 3, and is provided to the breathing region around the nose of the exerciser. Thereby, the particulate cleanliness of the gas in the breathing region can reach 0~20 μg/m³.

In addition, the main body 1 further includes a gas-flow channel 13 disposed between the gas inlet 11 and the gas outlet 12. The purification unit 2 is disposed in the gas-flow channel 13 for filtering the gas introduced into the gas-flow channel 13. The gas guider 3 is disposed in the gas-flow channel 13 and located at a side of the purification unit 2, so as to guide the gas inhaled through the at least one gas inlet 11 to flow through the purification unit 2 for filtering and purifying and discharge out through the at least one gas outlet 12. The gas detection module 4 is disposed in the gas-flow channel 13 for detecting the gas inhaled from the exercise environment outside the main body 1, so as to acquire the gas information and the particulate cleanliness. In this way, the gas detection module 4 can control the operations of the gas guider 3 to enable and/or disable the gas guider 3. When the gas guider 3 is operated in the enable state, the gas is inhaled through the at least one gas inlet 11, flows through the purification unit 2 for filtering and purifying, and is discharged out through the at least one gas outlet 12, so as to provide the filtered and purified gas to the breathing region around the nose of the exerciser for breathing.

The above-mentioned purification unit 2 disposed in the gas-flow channel 13 can be implemented in various embodiments. For example, as shown in FIG. 2A, the purification unit 2 is a high efficiency particulate air (HEPA) filter screen 2a. When the gas is introduced into the gas-flow channel 13 by the gas guider 3, the gas is filtered through the HEPA filter screen 2a to absorb the chemical smoke, bacteria, dust particles and pollen contained in the gas to achieve the effects of filtering and purifying the introduced gas 1. In some embodiments, the HEPA filter screen 2a is coated with a layer of chloride-dioxide clean factor which can inhibit viruses, bacteria, influenza A virus, influenza B virus, enterovirus or norovirus in the air with the inhibition rate over 99%. It is helpful for reducing the cross-infection of viruses. In other embodiments, the HEPA filter screen 2a is coated with an herbal protective layer extracted from ginkgo and Japanese *Rhus chinensis* to form an herbal protective anti-allergic filter, so as to resist allergy effectively and destroy a surface protein of influenza virus, such as H1N1 influenza virus, in the gas passing through the HEPA filter screen 2a. In some other embodiments, the HEPA filter screen 2a is coated with a silver ion to inhibit viruses and bacteria in the gas.

Figure 2B:
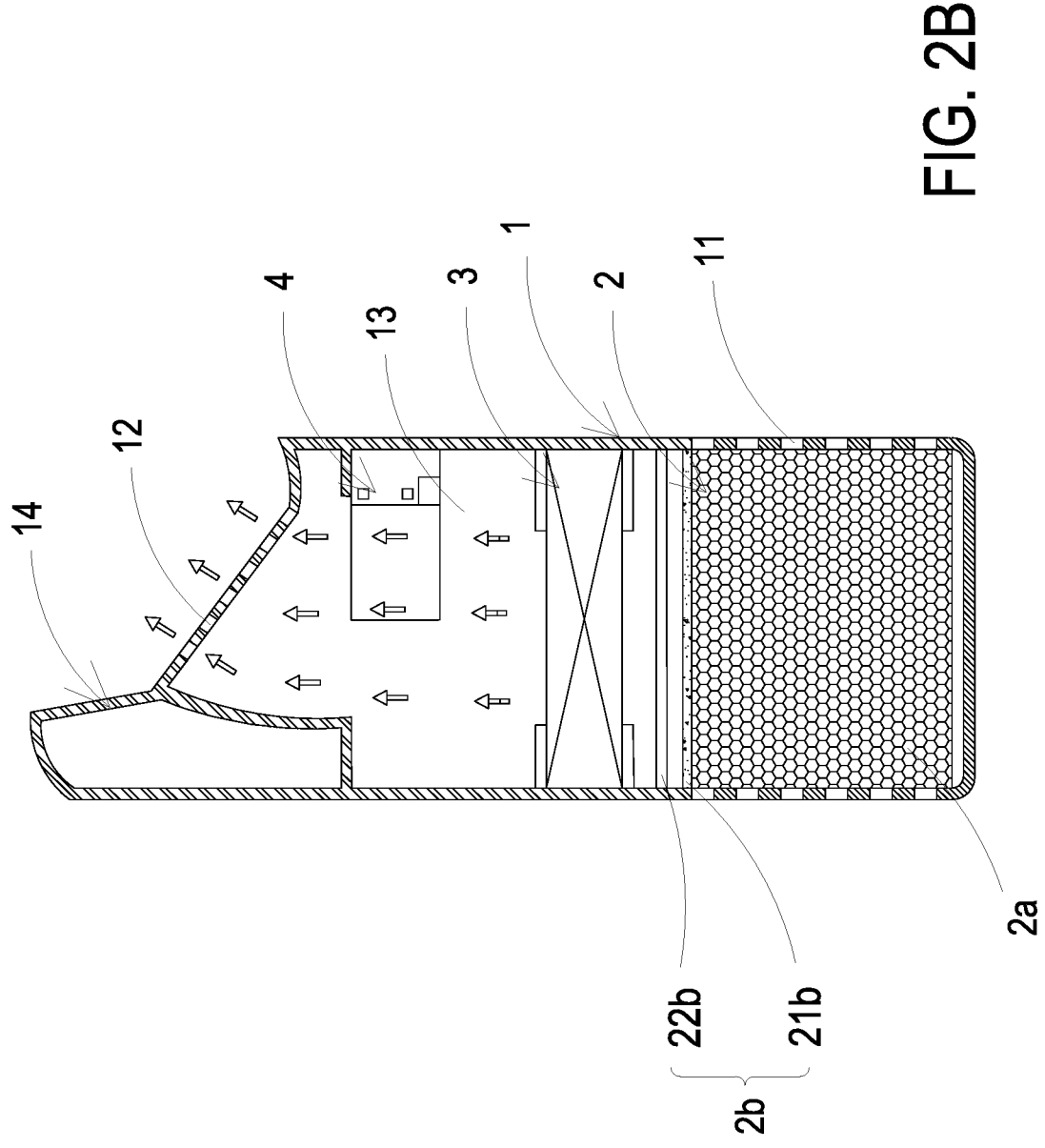
FIG. 2B is a cross-section view of a purification unit formed by the filter screen of FIG. 2A combined with a photo-catalyst unit.

As shown in FIG. 2B, in the embodiment, the purification unit 2 includes a photo-catalyst unit 2b combined with the HEPA filter screen 2a. The photo-catalyst unit 2b includes a photo-catalyst 21b and an ultraviolet lamp 22b. The photo-catalyst 21b and the ultraviolet lamp 22b are disposed in the gas-flow channel 13 respectively, and are spaced apart from each other at a distance. In the embodiment, the gas is introduced into the gas-flow channel 13 by the gas guider 3, and the photo-catalyst 21b is irradiated by the ultraviolet lamp 22b to convert light energy into chemical energy, thereby decomposing harmful gases and disinfecting bacteria contained in the gas, thereby achieving the effects of filtering and purifying the introduced gas.

Figure 2C:
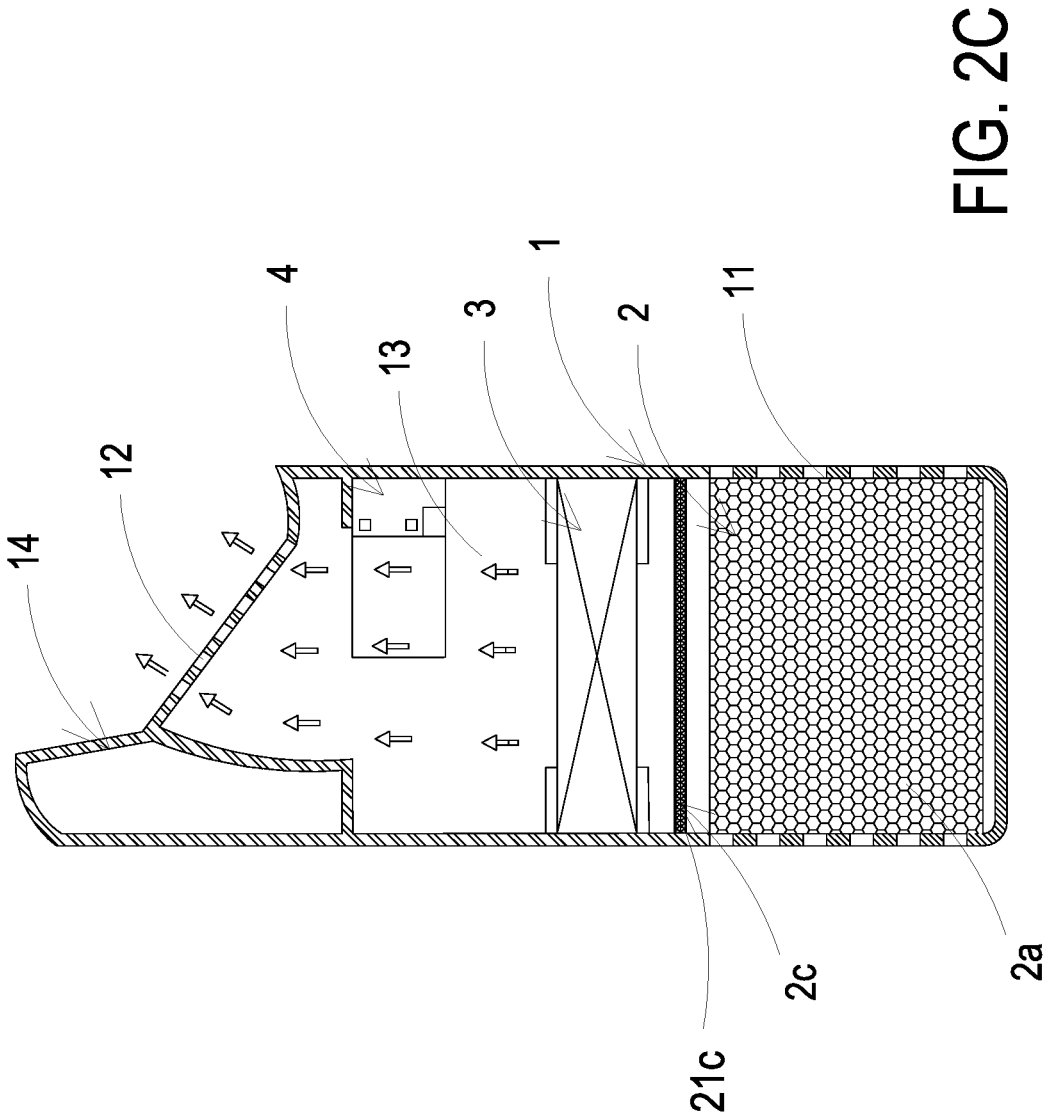
FIG. 2C is a cross-section view of a purification unit formed by the filter screen of FIG. 2A combined with a photo-plasma unit.

As shown in FIG. 2C, in the embodiment, the purification unit 2 includes a photo-plasma unit 2c combined with the HEPA filter screen 2a. The photo-plasma unit 2c includes a nanometer irradiation tube 21c. The nanometer irradiation tube 21c is disposed in the gas-flow channel 13. When the gas is introduced into the gas-flow channel 13 by the gas guider 3, the introduced gas is irradiated by the nanometer irradiation tube 21c, thereby decomposing oxygen mol- ecules and water molecules contained in the gas into an ion flow of high oxidizing photo-plasma which is capable of destroying organic molecules. Accordingly, gas molecules like volatile formaldehyde, volatile toluene and volatile organic compounds (VOC) contained in the gas are decom- posed into water and carbon dioxide, so as to achieve the effects of filtering and purifying the introduce gas.

Figure 2D:
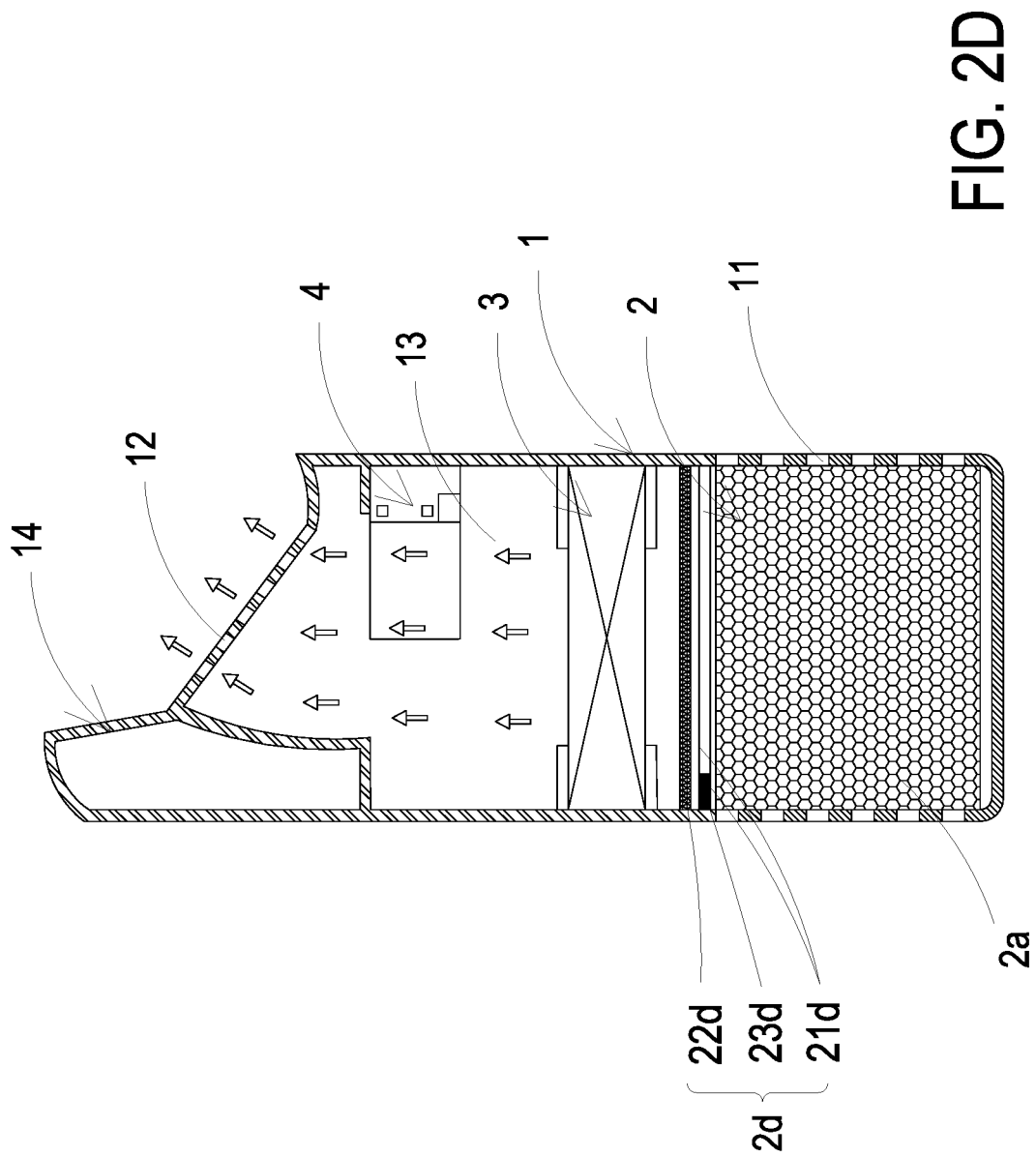
FIG. 2D is a cross-section view of a purification unit formed by the filter screen of FIG. 2A combined with a negative ionizer.

As shown in FIG. 2D, in the embodiment, the purification unit 2 includes a negative ionizer 2d combined with the HEPA filter screen 2a. The negative ionizer 2d includes at least one electrode wire 21d, at least one dust collecting plate 22d and a boost power supply device 23d. The at least one electrode wire 21d and the at least one dust collecting plate 22d are disposed within the gas-flow channel 13. As the at least one electrode wire 21d is provided with a high voltage by the boost power supply device 23d to discharge, the dust collecting plate 22d is carried with negative charge. When the gas is introduced into the gas-flow channel 13 by the gas guider 3, the at least one electrode wire 21d discharges and makes the particles in the gas carry with positive charges, therefore the particles having positive charges are adhered to the dust collecting plate 22d carried with negative charges, so as to achieve the effects of filtering and purifying the introduced gas.

Figure 2E:
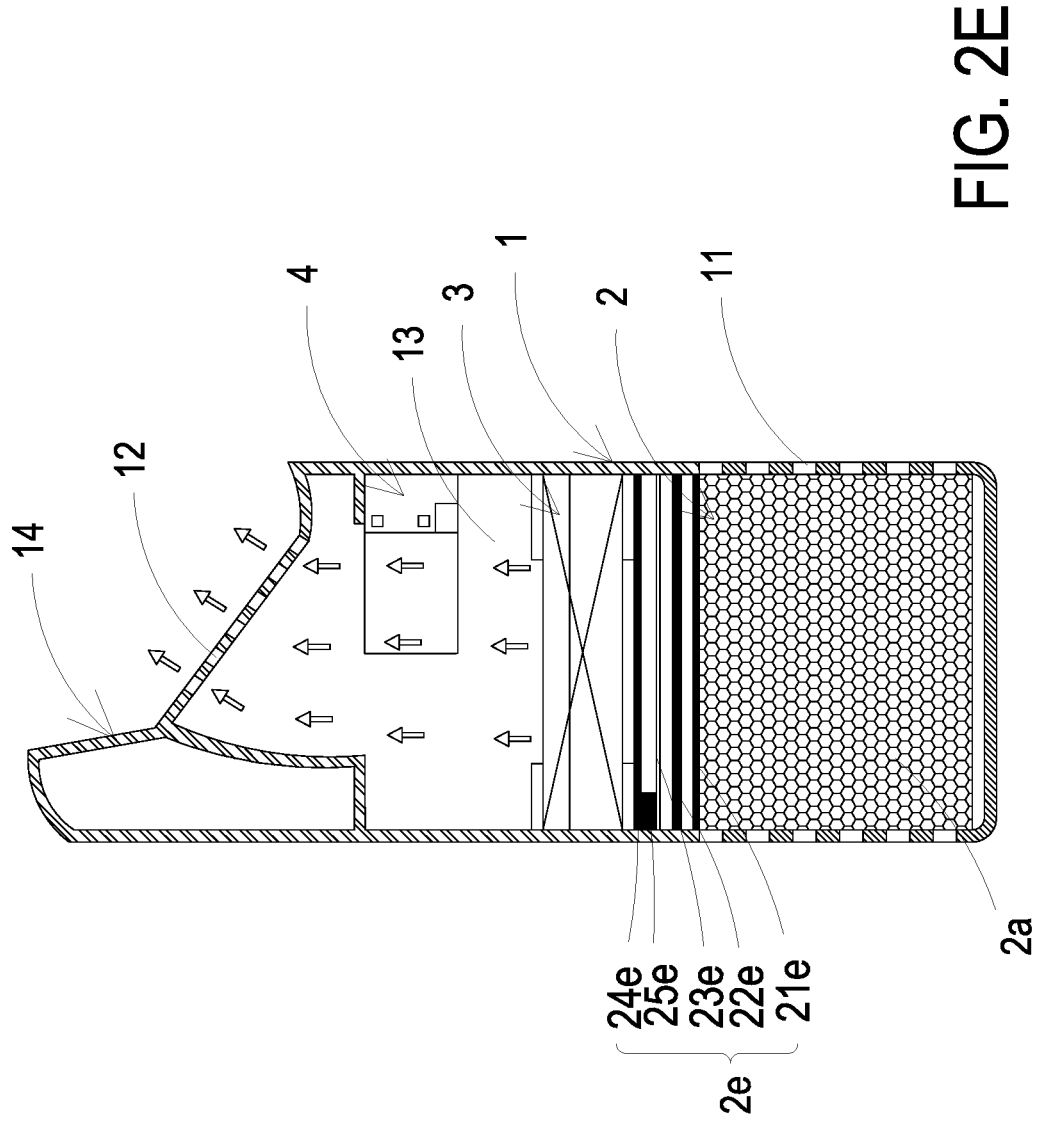
FIG. 2E is a cross-section view of a purification unit formed by the filter screen of FIG. 2A combined with a plasma ion unit.

As shown in FIG. 2E, in the embodiment, the purification unit 2 includes a plasma ion unit 2e combined with the HEPA filter screen 2a. The plasma ion unit 2e includes a first electric-field protection screen 21e, an adsorption filter screen 22e, a high-voltage discharge electrode 23e, a second electric-field protection screen 24e and a boost power supply device 25e. The first electric-field protection screen 21e, the adsorption filter screen 22e, the high-voltage discharge electrode 23e and the second electric-field protection screen 24e are disposed within the gas-flow channel 13. The adsorption filter screen 22e and the high-voltage discharge electrode 23e are disposed between the first electric-field protection screen 21e and the second electric-field protection screen 24e. As the high-voltage discharge electrode 23e is provided with a high voltage by the boost power supply device 25e to discharge, a high-voltage plasma column with plasma ion is generated. When the gas is introduced into the gas-guiding channel 13 by the gas guider 3, oxygen mol- ecules and water molecules contained in the gas are decom- posed into positive hydrogen ions ($H^+$) and negative oxygen ions ($O_2^-$) through the plasma ion. The substances attached with water around the ions are adhered on the surfaces of viruses and bacteria and converted into OH radicals. With their extremely strong oxidizing power, the OH radicals rapidly extract hydrogen (H) from the protein on the sur- faces of viruses and bacteria, thereby decomposing the protein and suppressing activity thereof, so as to remove the hydrogen atom (H) from this structure and inactivates the undesirable substance and achieve the effects of filtering and purifying the introduced gas.

Preferably but not exclusively, the gas guider 3 is a fan, such as a vortex fan or a centrifugal fan. Alternatively, as shown in FIGS. 3A, 3B, 4A and 4B, the gas guider 3 is an actuating pump 30. In the embodiment, the actuating pump 30 includes a gas inlet plate 301, a resonance plate 302, a piezoelectric actuator 303, a first insulation plate 304, a conducting plate 305 and a second insulation plate 306, which are sequentially stacked on each other. In the embodi- ment, the gas inlet plate 301 has at least one gas inlet aperture 301a, at least one convergence channel 301b and a convergence chamber 301c. The at least one gas inlet aperture 301a is disposed to inhale the gas. The at least one gas inlet aperture 301a correspondingly penetrates through the gas inlet plate 301 into the at least one convergence channel 301b, and the at least one convergence channel 301b is converged to the convergence chamber 301c. Accord- ingly, the gas inhaled through the at least one gas inlet aperture 301a is converged into the convergence chamber 301c. The number of the at least one gas inlet aperture 301a is the same as the number of the at least one convergence channel 301b. In the embodiment, the number of the at least one gas inlet aperture 301a and the number of the at least one convergence channel 301b are exemplified by four, but not limited thereto. The four gas inlet apertures 301a run through the gas inlet plate 301 into the four convergence channels 301b respectively, and the four convergence chan- nels 301b are converged to the convergence chamber 301c.

Figure 3A:
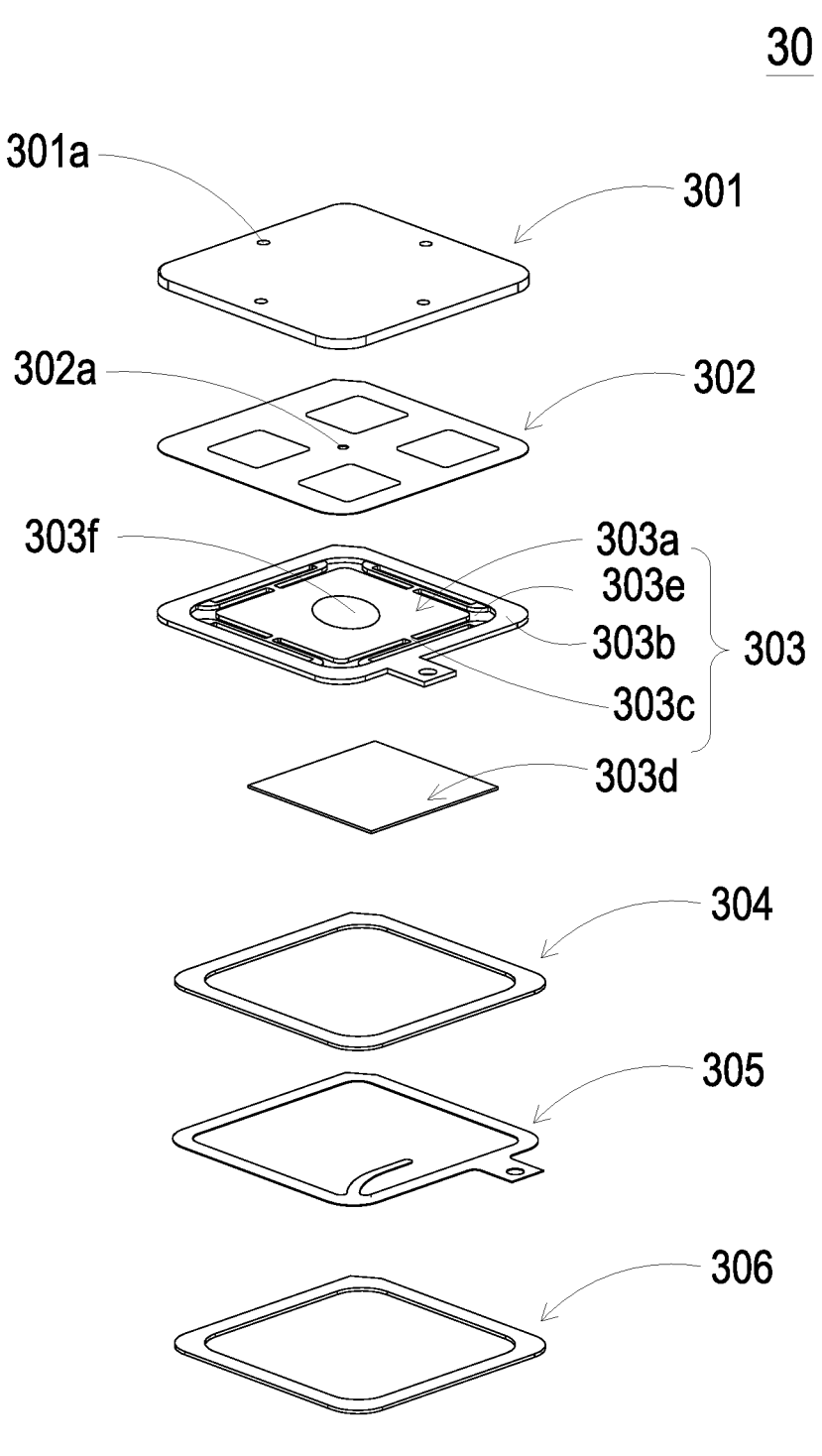
FIG. 3A is a schematic exploded front view of related components of a gas guider of the purification device of exercise environment of the present disclosure as the gas guider is an actuating pump.
Figure 3B:
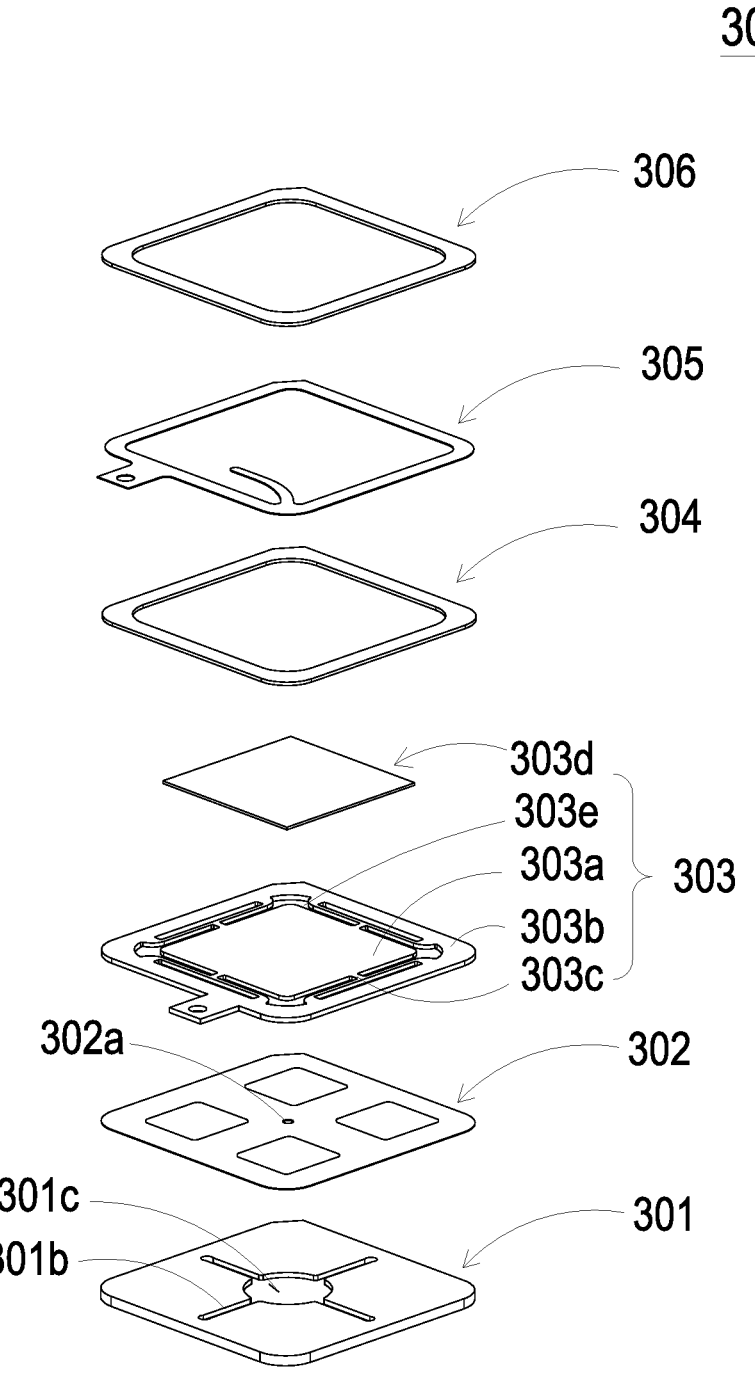
FIG. 3B is a schematic exploded rear view of related components of the gas guider of the purification device of exercise environment of the present disclosure as the gas guider is the actuating pump.
Figure 4A:
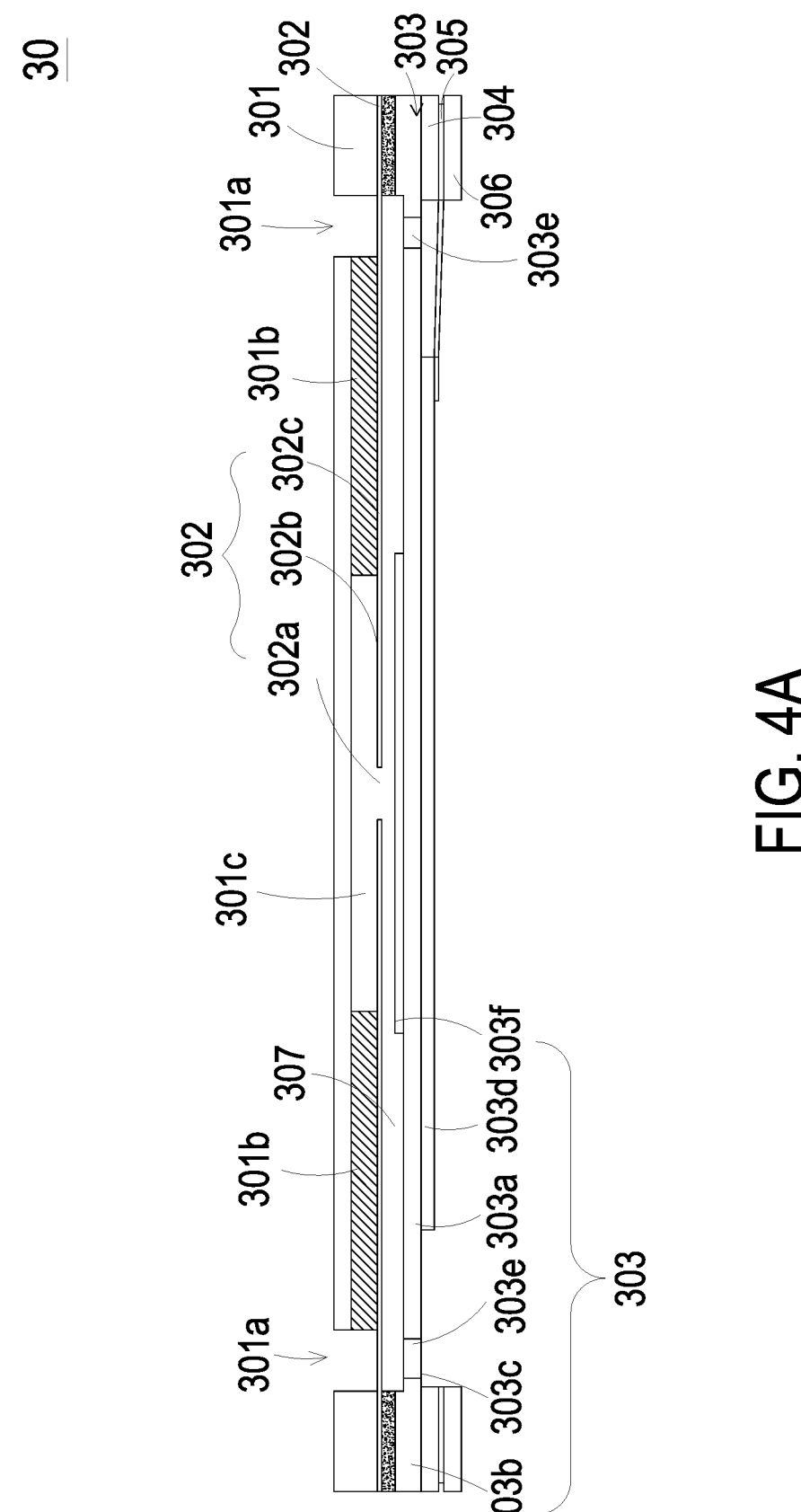
FIG. 4A is a cross-section view of the actuating pump of the purification device of exercise environment of the present disclosure.

Please refer to FIGS. 3A, 3B and 4A. The resonance plate 302 is attaching and assembling on the gas inlet plate 301. The resonance plate 302 has a central aperture 302a, a movable part 302b and a fixed part 302c. The central aperture 302a is located at a center of the resonance plate 302 and corresponding in position to the convergence cham- ber 301c of the gas inlet plate 301. The movable part 302b surrounds the central aperture 302a is corresponding in position to the convergence chamber 301c. The fixed part 302c is disposed around the periphery of the resonance plate 302 and firmly attached on the gas inlet plate 301.

As shown in FIGS. 3A, 3B and 4A. The piezoelectric actuator 303 includes a suspension plate 303a, an outer frame 303b, at least one bracket 303c, a piezoelectric element 303d, at least one vacant space 303e and a bulge 303f. The suspension plate 303a is square-shaped because the square suspension plate 303a is more power-saving than the circular suspension plate. Generally, the consumed power of the capacitive load at the resonance frequency is positive related to the resonance frequency. Since the reso- nance frequency of the square suspension plate 303a is obviously lower than that of the circular suspension plate, the consumed power of the square suspension plate 303a is lower. Therefore, the square suspension plate 303a of the present disclosure is more effective in power-saving. In the embodiment, the outer frame 303b is disposed around the periphery of the suspension plate 303a. The at least one bracket 303c is connected between the suspension plate 303a and the outer frame 303b for elastically supporting the suspension plate 303a. The piezoelectric element 303d has a side, and a length of the side of the piezoelectric element 303d is less than or equal to that of the suspension plate 303a. The piezoelectric element 303d is attaching on a surface of the suspension plate 303a. When a voltage is applied to the piezoelectric element 303d, the suspension plate 303a is driven to undergo the bending deformation by the piezoelectric element 303d. The at least one vacant space 303e is formed between the suspension plate 303a, the outer frame 303b and the at least one bracket 303c for allowing the gas to flow therethrough. The bulge 303f is formed on a surface of the suspension plate 303a opposite to the surface of the suspension plate 303a attached with the piezoelectric element 303d. In the embodiment, the bulge 303f may be formed by using an etching process on the suspension plate 303a. Accordingly, the bulge 303f on the suspension plate 303a is integrally formed with and protrudes from the surface opposite to the surface attached with the piezoelectric element 303d, and formed a stepped structure.

Please continue referring to FIGS. 3A, 3B and 4A. In the embodiment, the gas inlet plate 301, the resonance plate 302, the piezoelectric actuator 303, the first insulation plate 304, the conducting plate 305 and the second insulation plate 306 are stacked and assembled sequentially. A chamber space 307 is formed between the suspension plate 303a and the resonance plate 302, and the chamber space 307 can be formed by filling a gap between the resonance plate 302 and the outer frame 303b of the piezoelectric actuator 303 with a material, such as a conductive adhesive, but not limited thereto. Thus, a specific depth between the resonance plate 302 and the suspension plate 303a is maintained to form the chamber space 307 and allow the gas to pass rapidly. In addition, since a suitable distance between the resonance plate 302 and the suspension plate 303a is maintained, the contact interference therebetween is reduced, and the noise caused thereby is largely reduced. In some other embodiments, the thickness of the conductive adhesive filled in the gap between the resonance plate 302 and the outer frame 303b of the piezoelectric actuator 303 can be reduced by increasing the height of the outer frame 303b of the piezoelectric actuator 303. Therefore, the entire assembling structure of actuating pump 30 would not indirectly influenced by the impact on the filling material of the hot pressing temperature and the cooling temperature, so as to avoid the actual size of the formed chamber space 307 being influenced by the thermal expansion and cooling contraction of the filling material, i.e., conductive adhesive, but not limited thereto. In addition, since the transportation effect of the actuating pump 30 is affected by the chamber space 307, maintaining a constant chamber space 307 is very important to provide a stable transportation efficiency of the actuating pump 30.

Figure 4B:
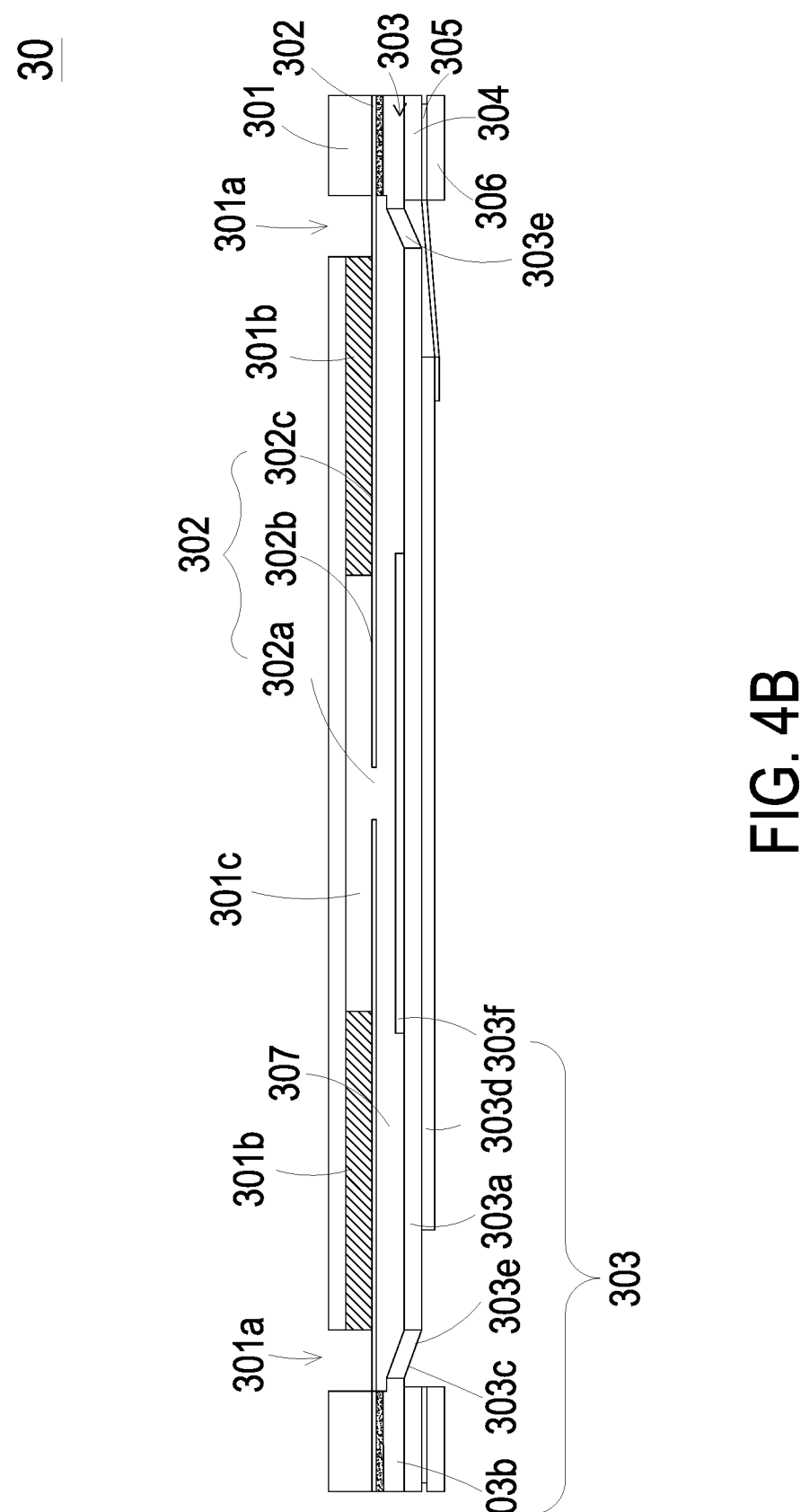
FIG. 4B is a cross-section view of an actuating pump of the purification device of exercise environment according to another embodiment of the present disclosure.

Please refer to FIG. 4B, in some other embodiments of the piezoelectric actuator 303, the suspension plate 303a is formed by stamping to make it extend outwardly a distance. The extended distance can be adjusted through the at least one bracket 303c formed between the suspension plate 303a and the outer frame 303b. Consequently, the surface of the bulge 303f disposed on the suspension plate 303a and the surface of the outer frame 303b are non-coplanar. By applying a small amount of filling materials, such as a conductive adhesive, to the coupling surface of the outer frame 303b, the piezoelectric actuator 303 is attached to the fixed part 302c of the resonance plate 302 by hot pressing, thereby assembling the piezoelectric actuator 303 and the resonance plate 302 in combination. Thus, the structure of the chamber space 307 is improve by directly stamping the suspension plate 303a of the piezoelectric actuator 303 described above. In this way, the required chamber space 307 can be obtained by adjusting the stamping distance of the suspension plate 303a of the piezoelectric actuator 303, thereby simplifying the structural design of the chamber space 307 and achieving the advantages of simplifying the manufacturing process and shortening the processing time. In addition, the first insulation plate 304, the conducting plate 305 and the second insulation plate 306 are all thin frame-shaped sheets, but are not limited thereto, and are sequentially stacked on the piezoelectric actuator 303 to complete the entire structure of actuating pump 30.

Figure 4C:
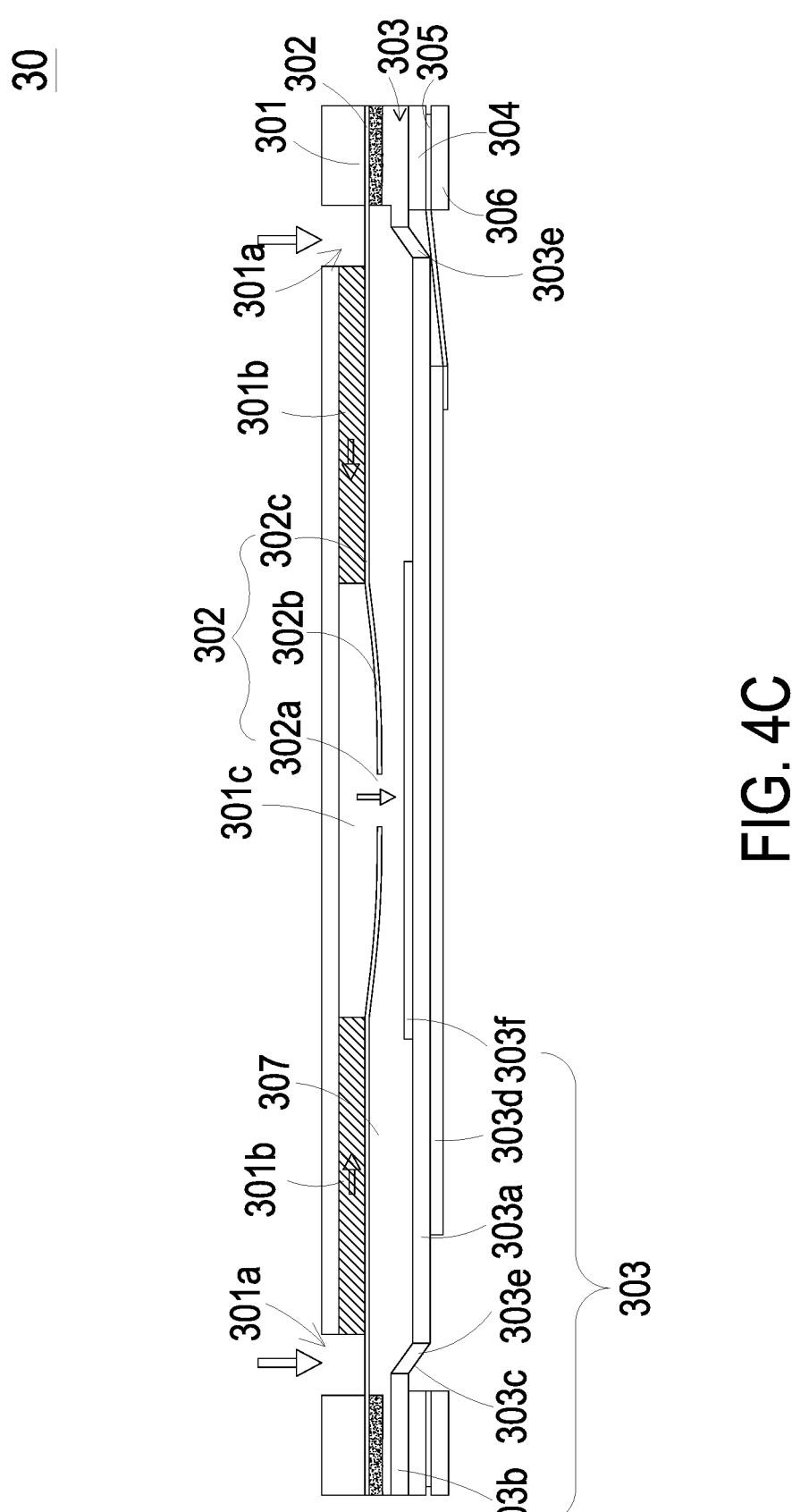
FIGS. 4C to 4E schematically illustrate the operation steps of the actuating pump of FIG. 4A.
Figure 4D:
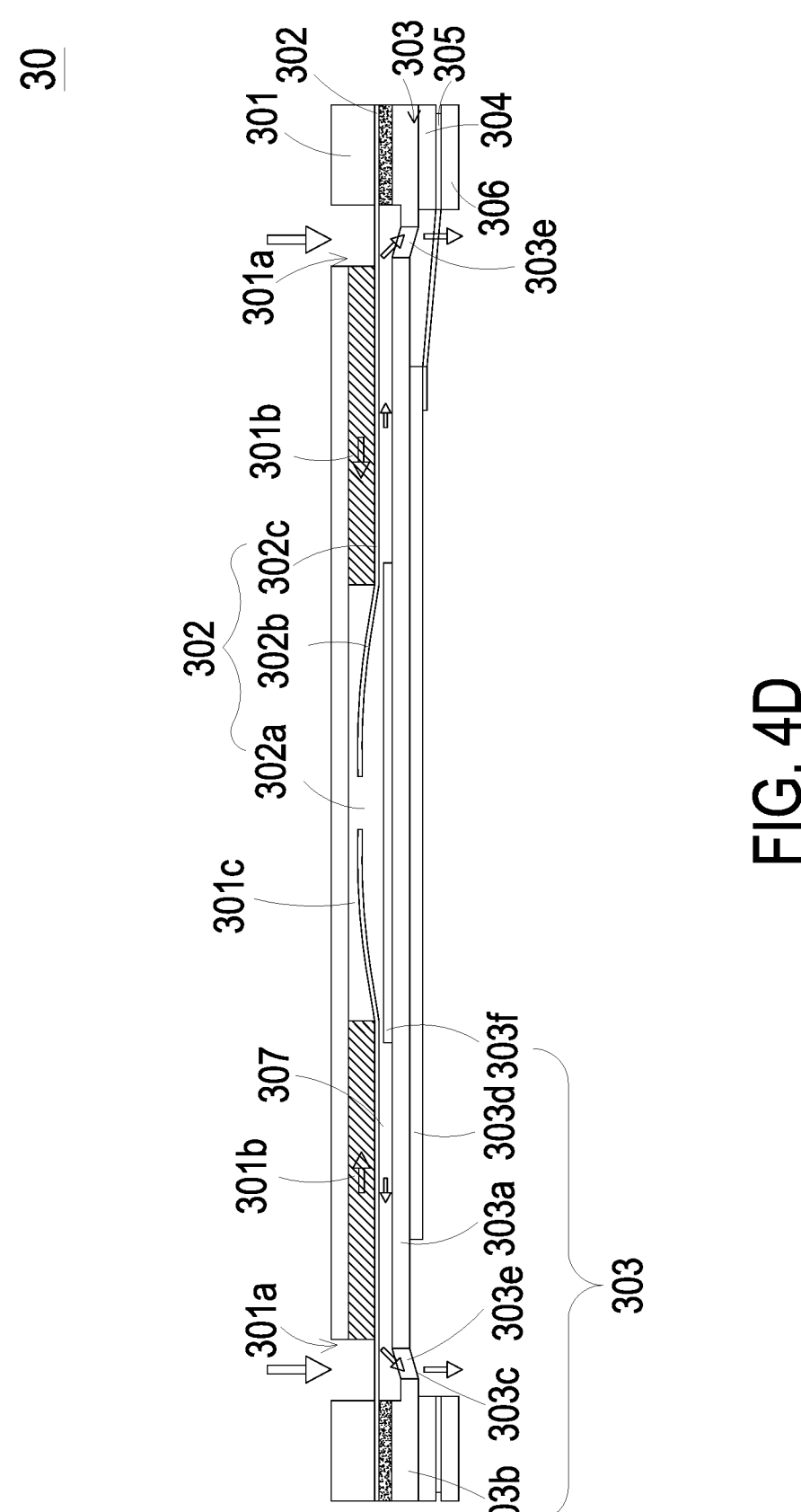
Figure 4E:
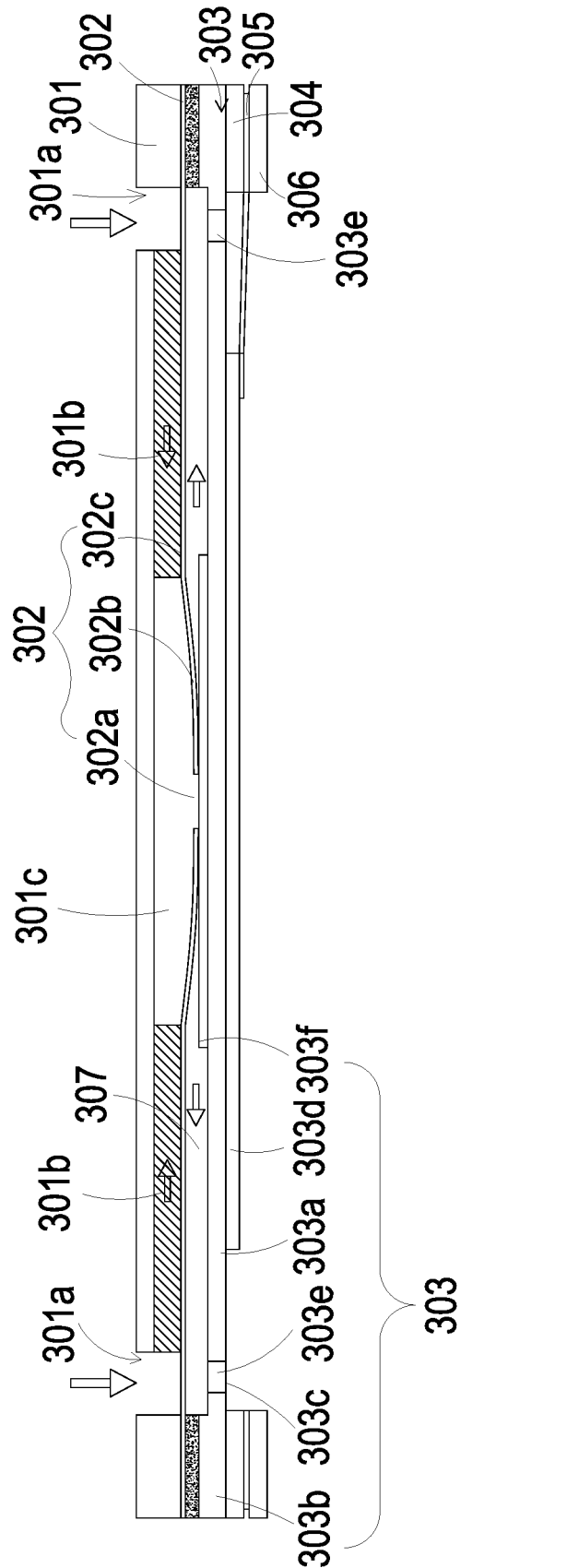

In order to understand the operation steps of the actuating pump 30, please refer to FIGS. 4C to 4E. Please refer to FIG.

4C, the piezoelectric element 303d of the piezoelectric actuator 303 is deformed after a driving voltage is applied thereto, the suspension plate 303a is driven to displace downwardly. In that, the volume of the chamber space 307 is increased and a negative pressure is generated in the chamber space 307, and the gas in the convergence chamber 301c is introduced into the chamber space 307. At the same time, the resonance plate 302 is displaced downwardly and synchronously in resonance with the suspension plate 303a. Thereby, the volume of the convergence chamber 301c is increased. Since the gas in the convergence chamber 301c is introduced into the chamber space 307, the convergence chamber 301c is also in a negative pressure state, and therefore the gas is sucked into the convergence chamber 301c through the gas inlet apertures 301a and the convergence channels 301b. Then, as shown in FIG. 4D, the piezoelectric element 303d drives the suspension plate 303a to displace upwardly to compress the chamber space 307. Similarly, the resonance plate 302 is actuated in resonance with the suspension plate 303a and is displaced upwardly. Thus, the gas in the chamber space 307 is further transported downwardly to pass through the vacant spaces 303e, thereby achieve the effect of gas transportation. Finally, as shown in FIG. 4E, when the suspension plate 303a is driven and returns to an initial state, the resonance plate 302 is also driven to displace downwardly due to inertia. In that, the resonance plate 302 pushes the gas in the chamber space 307 toward the vacant spaces 303e, and increases the volume of the convergence chamber 301c. Thus, the gas can continuously pass through the gas inlet apertures 301a and the convergence channels 301b, and then converged in the convergence chamber 301c. By repeating the operation steps illustrated in FIGS. 4C to 4E continuously, the actuating pump 30 can continuously transport the gas at high speed. The gas enters the gas inlet apertures 301a, flows through a flow path formed by the gas inlet plate 301 and the resonance plate 302 and generates a pressure gradient, and then transported downwardly through the vacant spaces 303e. Thus, the fluid can flow at a high speed and complete the fluid transporting operation of the actuating pump 30d.

Please refer to FIG. 5A to FIG. 5C, FIG. 6A to FIG. 6B, FIG. 7, FIG. 8A to FIG. 8B and FIG. 13. In the embodiment, the gas detection module 4 includes a controlling circuit board 4a, a gas detection main part 4b, a microprocessor 4c, a communicator 4d, a power unit 4e and a battery 4f The gas detection main part 4b, the microprocessor 4c, the communicator 4d and the power unit 4e are integrally packaged on the controlling circuit board 4a and are electrically connected to the controlling circuit board 4a. The power unit 4e provides the gas detection main part 4b with the power for starting operation so that the gas detection main part 4b is able to detects the gas introduced from the outside of the main body 1 and acquires the gas information. Moreover, the power unit 4e is electrically connected to the battery 4f for receiving power. The microprocessor 4c receives the gas information and the particulate cleanliness for calculating and processing, and controls to enable and/or disable the operation of the gas guider 3 for purifying the gas. The communicator 4d receives the gas information and the particulate cleanliness from the microprocessor 4c, and then transmits the gas information and the particulate cleanliness to an external device 5 through a communication transmission. Accordingly, the external device 5 receives the gas information and provides a notification or an alarm. The external device 5 may be a mobile device, a cloud processing device or a computer system. The external communication transmission of the communicator 4d mentioned above may be a wired communication transmission (e.g., USB communication transmission) or a wireless communication transmission (e.g., Wi-Fi communication transmission, Bluetooth communication transmission, radio frequency identification (RFID) communication transmission, or near-field communication (NFC)).

Figure 11A:
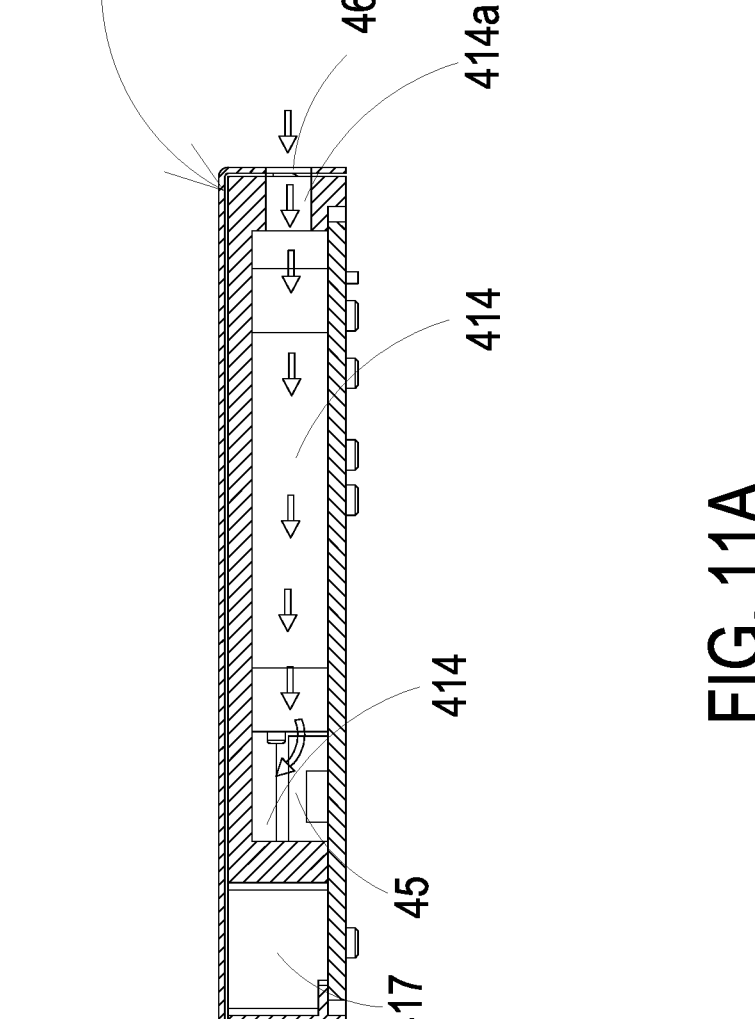
FIGS. 11A to 11C schematically illustrate gas flowing paths of the gas detection main part.

As shown in FIG. 5A to FIG. 5C, FIG. 6A to FIG. 6B, FIG. 7, FIG. 8A to FIG. 8B, FIG. 9A to FIG. 9B and FIG. 11A to FIG. 11C, in the embodiment, the gas detection main part 4b includes a base 41, a piezoelectric actuating element 42, a driving circuit board 43, a laser component 44, a particulate sensor 45 and an outer cover 46. The base 41 includes a first surface 411, a second surface 412, a laser loading region 413, a gas-inlet groove 414, a gas-guiding-component loading region 415 and a gas-outlet groove 416. The first surface 411 and the second surface 412 are two surfaces opposite to each other. The laser loading region 413 is hollowed out from the first surface 411 to the second surface 412. In addition, the outer cover 46 covers the base 41 and has a side plate 461, and the side plate 461 has an inlet opening 461a and an outlet opening 461b. The gas-inlet groove 414 is concavely formed on the second surface 412 and is disposed neighboring to the laser loading region 413. The gas-inlet groove 414 includes a gas-inlet 414a and two side walls. The gas-inlet 414a is in communication with a space outside the base 41, and corresponds in position to the inlet opening 461a of the outer cover 46. A transparent window 414b is opened on the two side walls and is in communication with the laser loading region 413. Therefore, the first surface 411 of the base 41 is covered and attached by the outer cover 46, and the second surface 412 is covered and attached by the driving circuit board 43. Thus, the gas-inlet groove 414 defines a gas-inlet path, as shown in FIG. 7 and FIG. 11A.

Figure 6A:
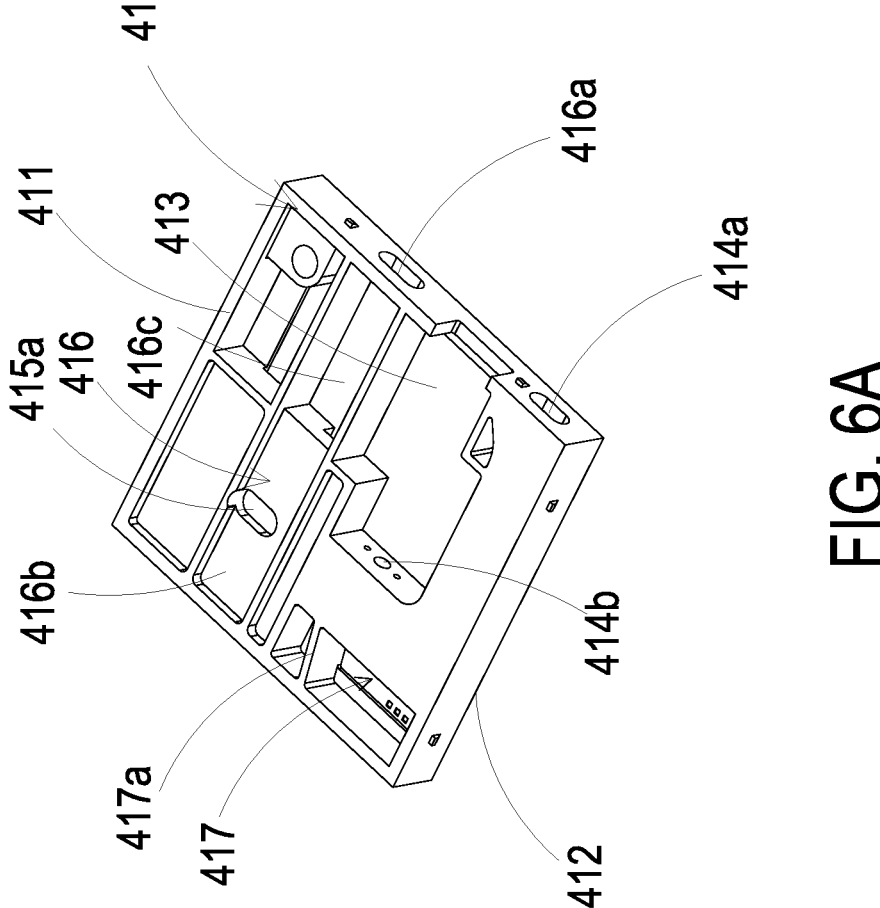
FIG. 6A is a schematic perspective view illustrating a base of the gas detection main part of the present disclosure.
Figure 6B:
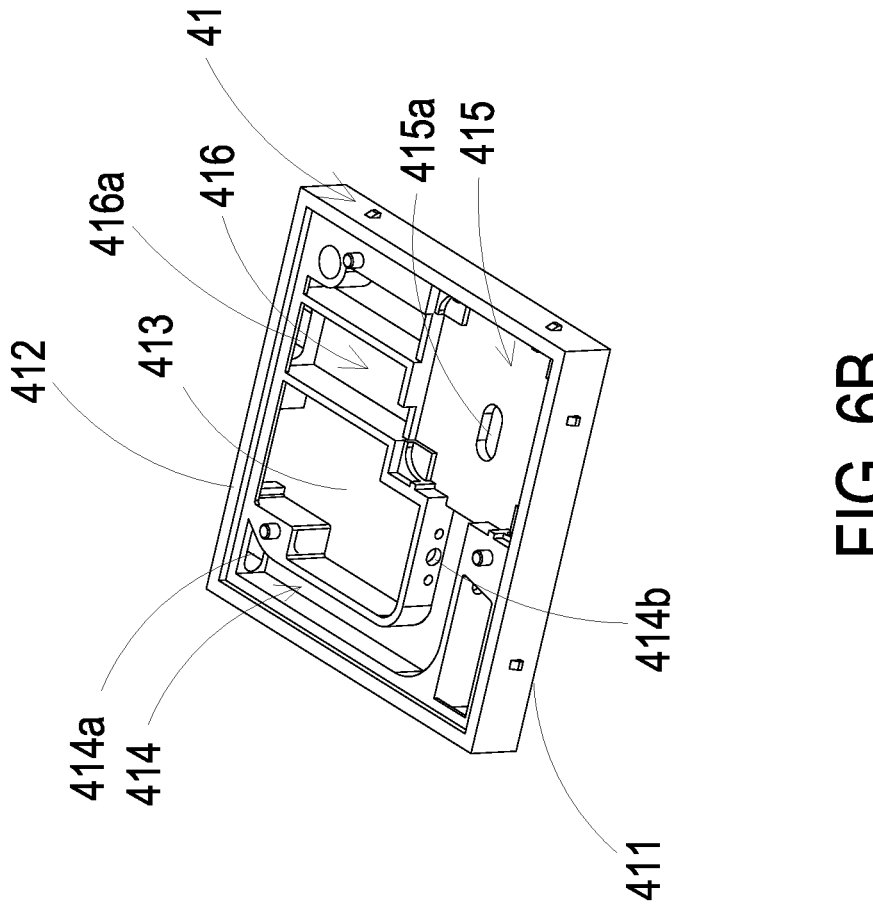
FIG. 6B is a schematic perspective view illustrating the base of the gas detection main part of the present disclosure from another perspective angle.

Please refer to FIGS. 6A to 6B. In the embodiment, the gas-guiding-component loading region 415 is concavely formed on the second surface 412 and is in fluid communication with the gas-inlet groove 414. A ventilation hole 415a penetrates a bottom surface of the gas-guiding-component loading region 415. The gas-outlet groove 416 includes a gas-outlet 416a, and the gas-outlet 416a is spatially corresponding to the outlet opening 461b of the outer cover 46. The gas-outlet groove 416 includes a first section 416b and a second section 416c. The first section 416b is concavely formed on a region of the first surface 411 spatially corresponding to a vertical projection area of the gas-guiding-component loading region 415. The second section 416c is hollowed out from the first surface 411 to the second surface 412 in a region where the first surface 411 is not aligned with the vertical projection area of the gas-guiding-component loading region 415 and extended therefrom. The first section 416b and the second section 416c are connected to form a stepped structure. Moreover, the first section 416b of the gas-outlet groove 416 is in fluid communication with the ventilation hole 415a of the gas-guiding-component loading region 415, and the second section 416c of the gas-outlet groove 416 is in fluid communication with the gas-outlet 416a. In that, when the first and second surfaces 411 and 412 of the base 41 are attached and covered by the outer cover 46 and the driving circuit board 43 respectively, the gas-outlet groove 416 and the driving circuit board 43 defines a gas-outlet path collaboratively, as shown in FIG. 7 to FIG. 11C.

Figure 5A:
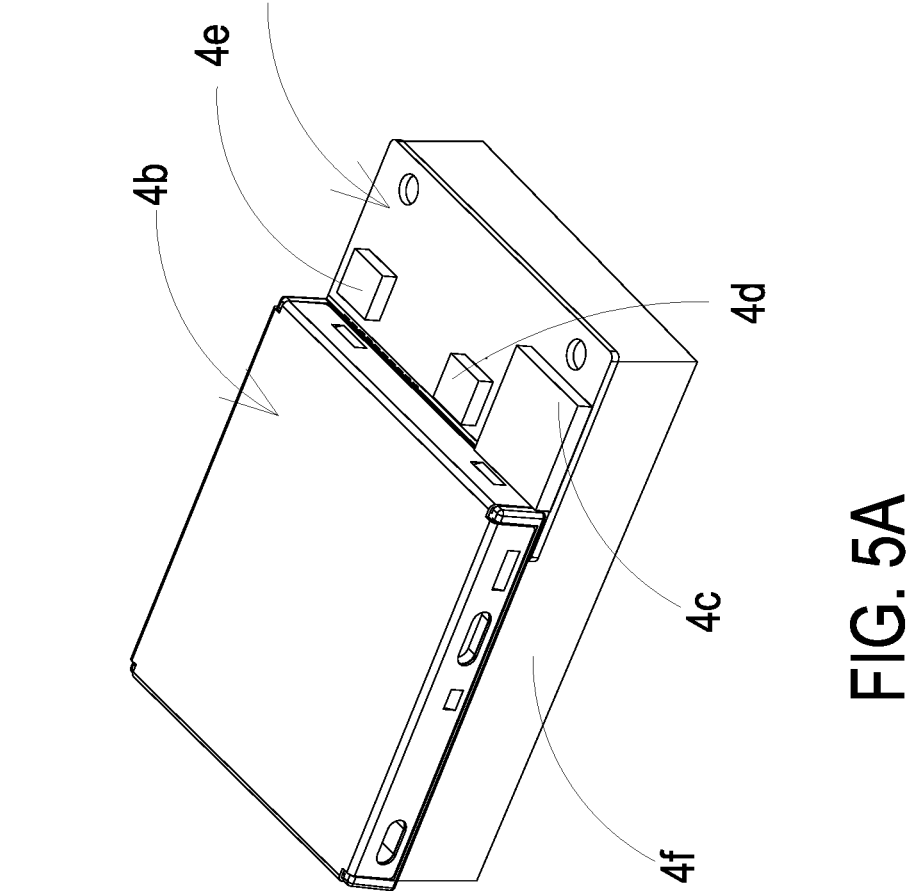
FIG. 5A is a schematic exterior view illustrating a gas detection module of the present disclosure.
Figure 5B:
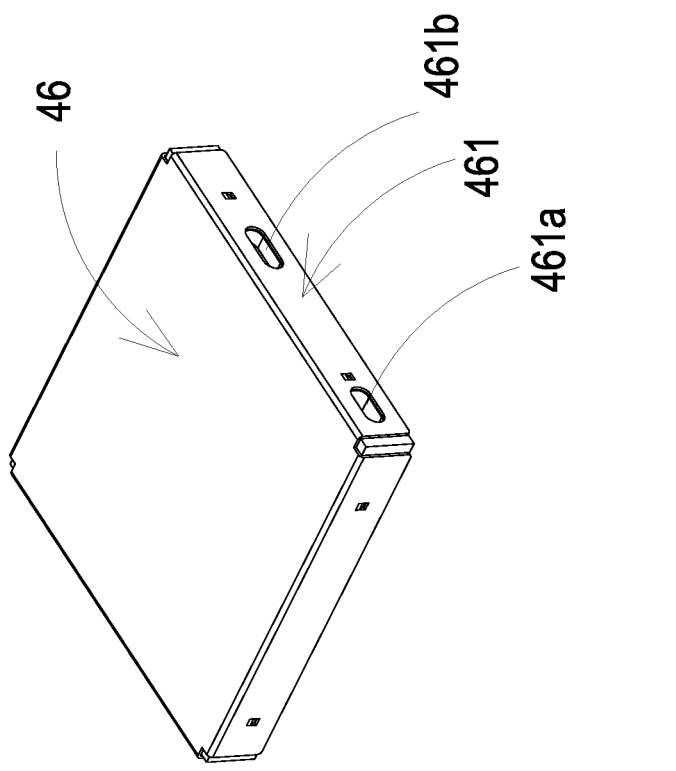
FIG. 5B is a schematic exterior view illustrating a gas detection main part of FIG. 5A.
Figure 5C:
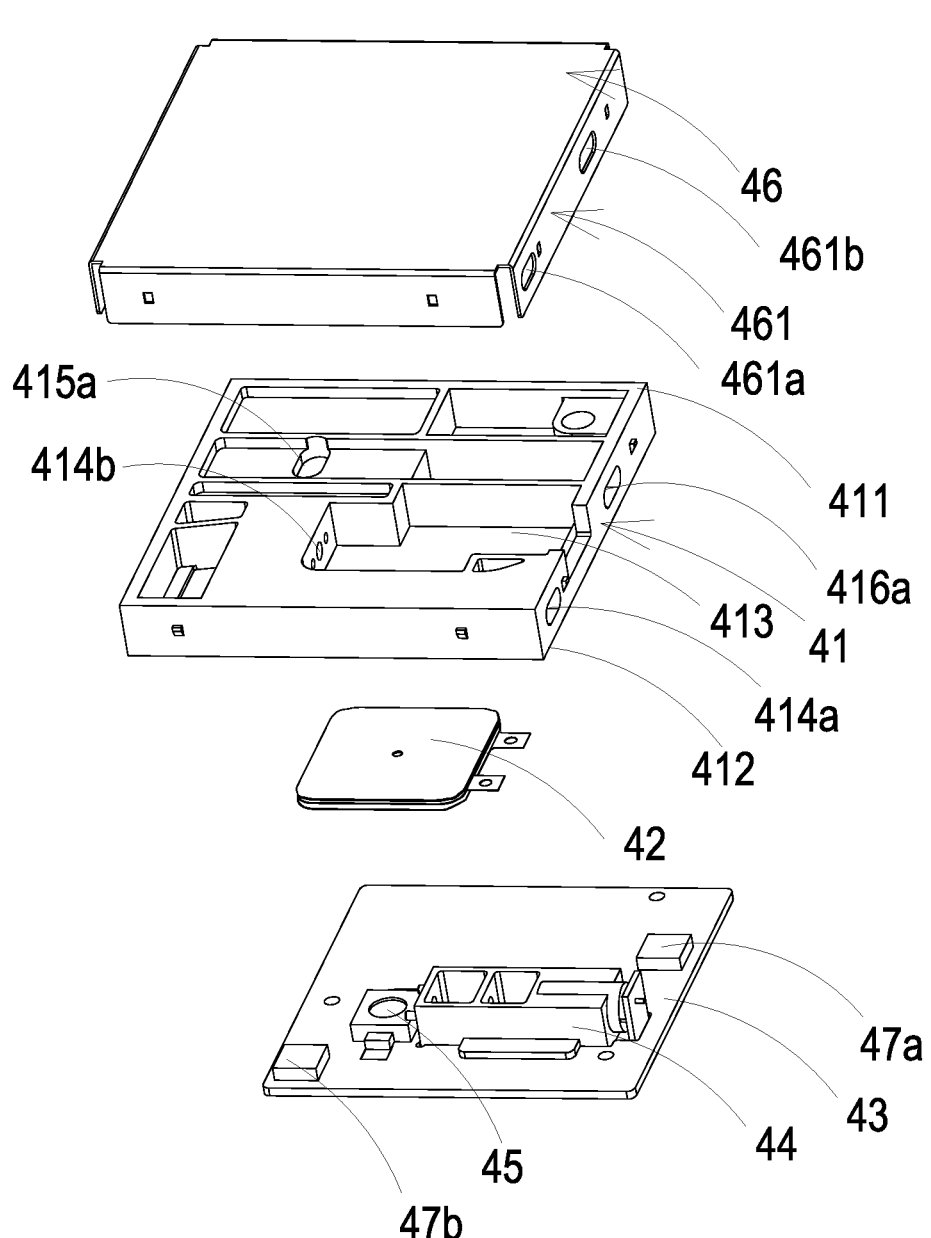
FIG. 5C is a schematic exploded view illustrating the gas detection main part of FIG. 5A.
Figure 7:
FIG. 7 is a schematic perspective view illustrating a laser component and a particulate sensor accommodated in the base of the gas detection main part of the present disclosure.
Figure 7:
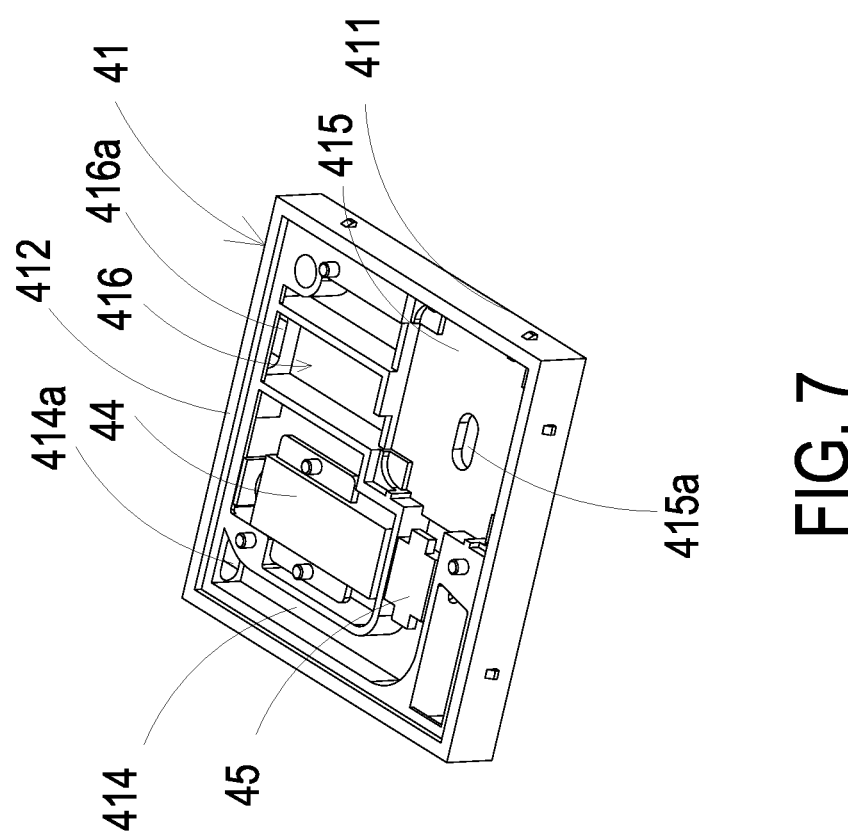

Please refer to FIG. 5C and FIG. 7. In the embodiment, the laser component 44 and the particulate sensor 45 are disposed on the driving circuit board 43 and are accommodated in the base 41. In order to describe the positions of the laser component 44, the particulate sensor 45 and the base 41 clearly, the driving circuit board 43 is omitted in FIG. 7. Please refer to FIG. 5C, FIG. 6B and FIG. 7. In the embodiment, the laser component 44 is accommodated in the laser loading region 413 of the base 41, and the particulate sensor 45 is accommodated in the gas-inlet groove 414 of the base 41 and is aligned with the laser component 44. In addition, the laser component 44 spatially is corresponding to the transparent window 414b, a light beam emitted by the laser component 44 passes through the transparent window 414b and irradiates into the gas-inlet groove 414. A path of the light beam emitted by the laser component 44 passes through the transparent window 414b and extends in a direction perpendicular to the gas-inlet groove 414. In the embodiment, the light beam emitted by the laser component 44 passes through the transparent window 414b and enters the gas-inlet groove 414, and suspended particles contained in the gas within the gas-inlet groove 414 is irradiated by the light beam. When the light beam irradiates on the suspended particles contained in the gas, the light beam is scattered and generates light spots. Meanwhile, the scattered light spots generated by scattering are received and calculated by the particulate sensor 45 located at a position where the gas-inlet groove 414 and the path of the light beam are orthogonal intersection, thereby obtaining related information about the size and concentration of the suspended particles contained in the gas. For example, the suspended particles contained in the gas include bacteria and viruses. In the embodiment, the particulate sensor 45 is a PM2.5 sensor.

Figure 8A:
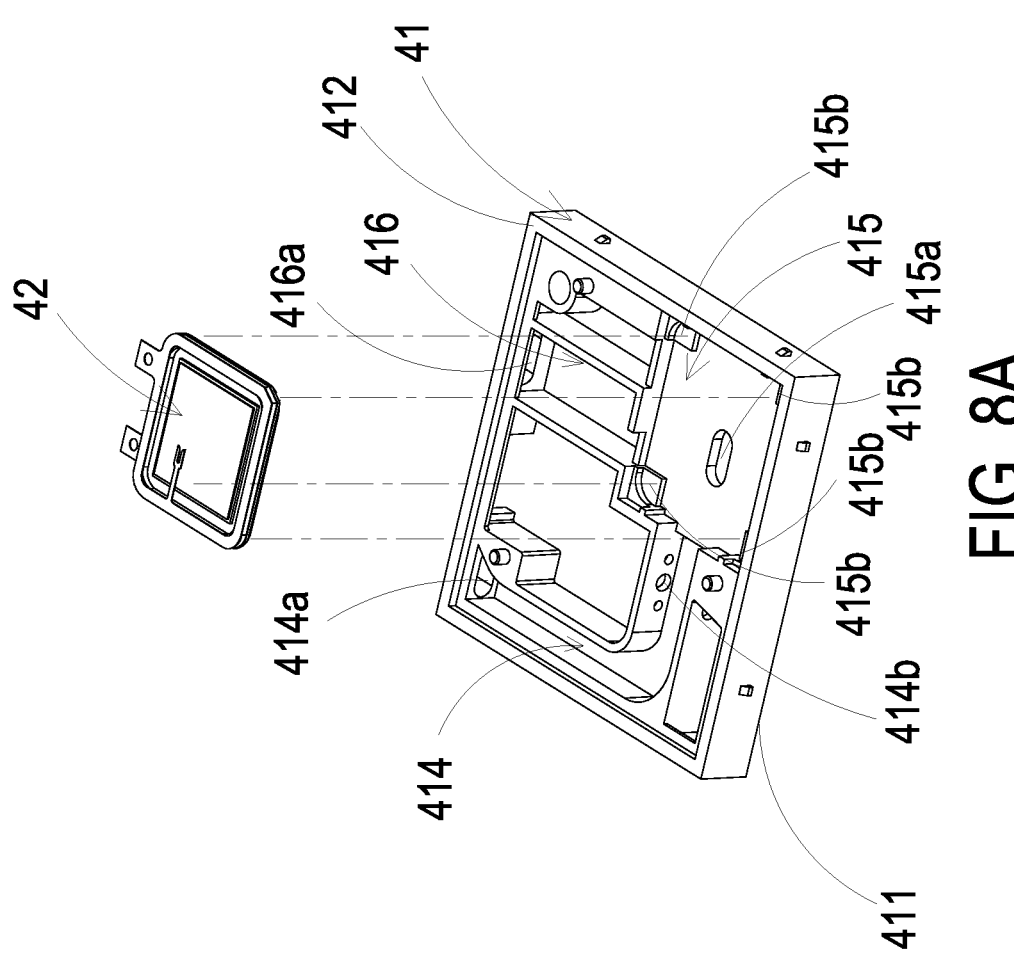
FIG. 8A is a schematic exploded view illustrating the combination of the piezoelectric actuator and the base of the gas detection main part of the present disclosure.
Figure 8B:
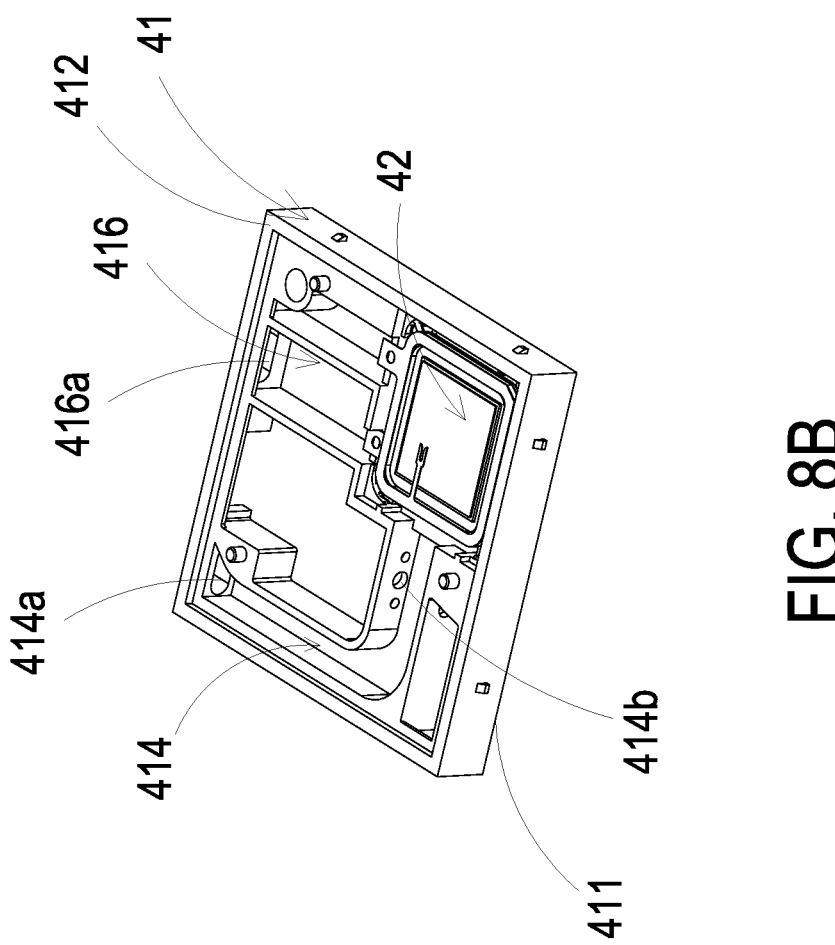
FIG. 8B is a schematic perspective view illustrating the combination of the piezoelectric actuator and the base of the gas detection main part of the present disclosure.

Please refer to FIG. 8A and FIG. 8B. The piezoelectric actuating element 42 is accommodated in the gas-guiding-component loading region 415 of the base 41. Preferably but not exclusively, the gas-guiding-component loading region 415 is square-shaped and includes four positioning protrusions 415b disposed at four corners of the gas-guiding-component loading region 415 respectively. The piezoelectric actuating element 42 is disposed in the gas-guiding-component loading region 415 through the four positioning protrusions 415b. In addition, as shown in FIGS. 6A, 6B, 11B and 11C, the gas-guiding-component loading region 415 is in fluid communication with the gas-inlet groove 414. When the piezoelectric actuating element 42 is enabled, the gas in the gas-inlet groove 414 is inhaled into the piezoelectric actuating element 42, and the gas is transported to the gas-outlet groove 416 through the ventilation hole 415a of the gas-guiding-component loading region 415.

Figure 11B:
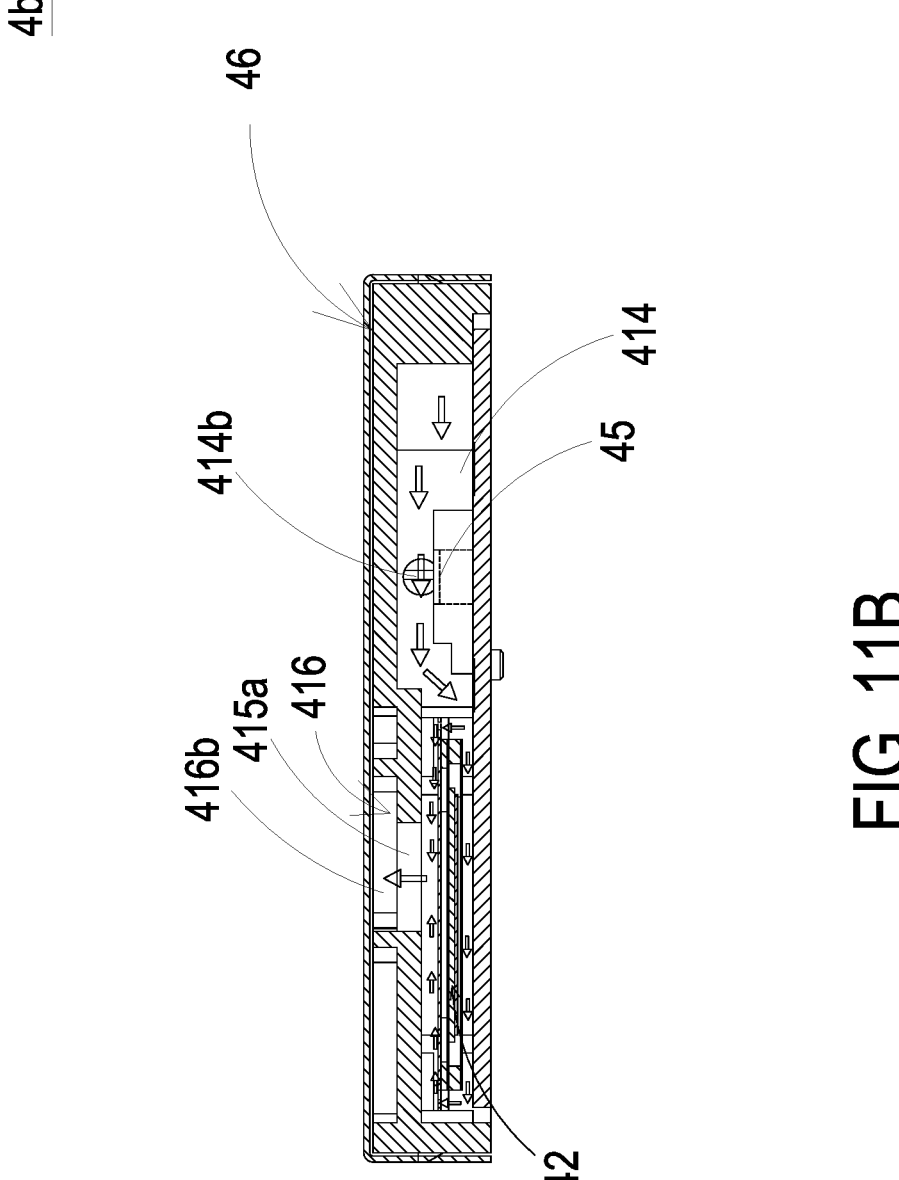
Figure 11C:
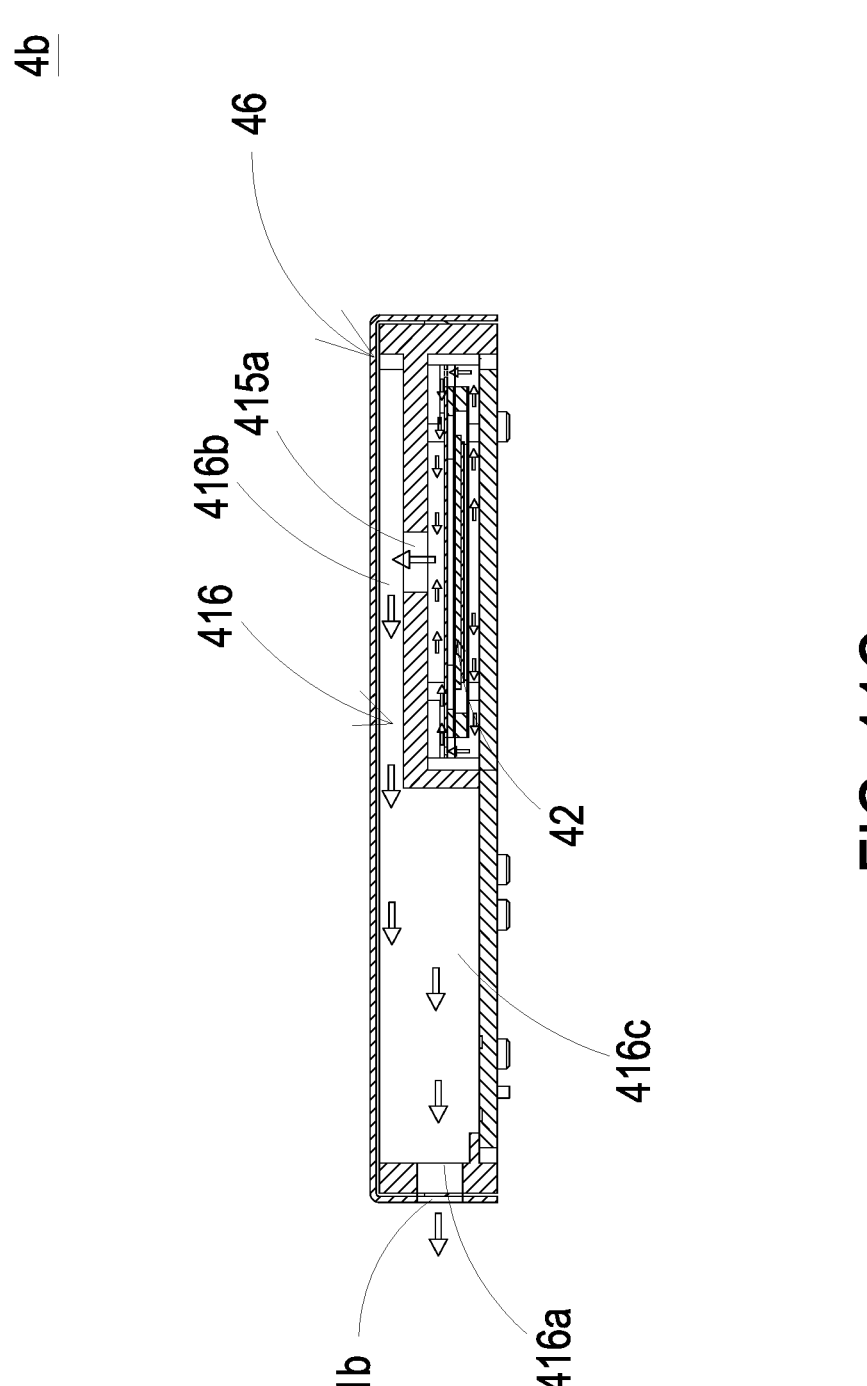

Please refer to FIGS. 5B and 5C. In the embodiment, the driving circuit board 43 covers and attaches on the second surface 412 of the base 41. The laser component 44 is disposed on and electrically connected to the driving circuit board 43. The particulate sensor 45 is disposed on and electrically connected to the driving circuit board 43. As shown in FIG. 5B, when the outer cover 46 covers the base 41, the inlet opening 461a is spatially corresponding to the gas-inlet 414a of the base 41 (as shown in FIG. 11A), and the outlet opening 461b is spatially corresponding to the gas-outlet 416a of the base 41 (as shown in FIG. 11C).

Figure 9A:
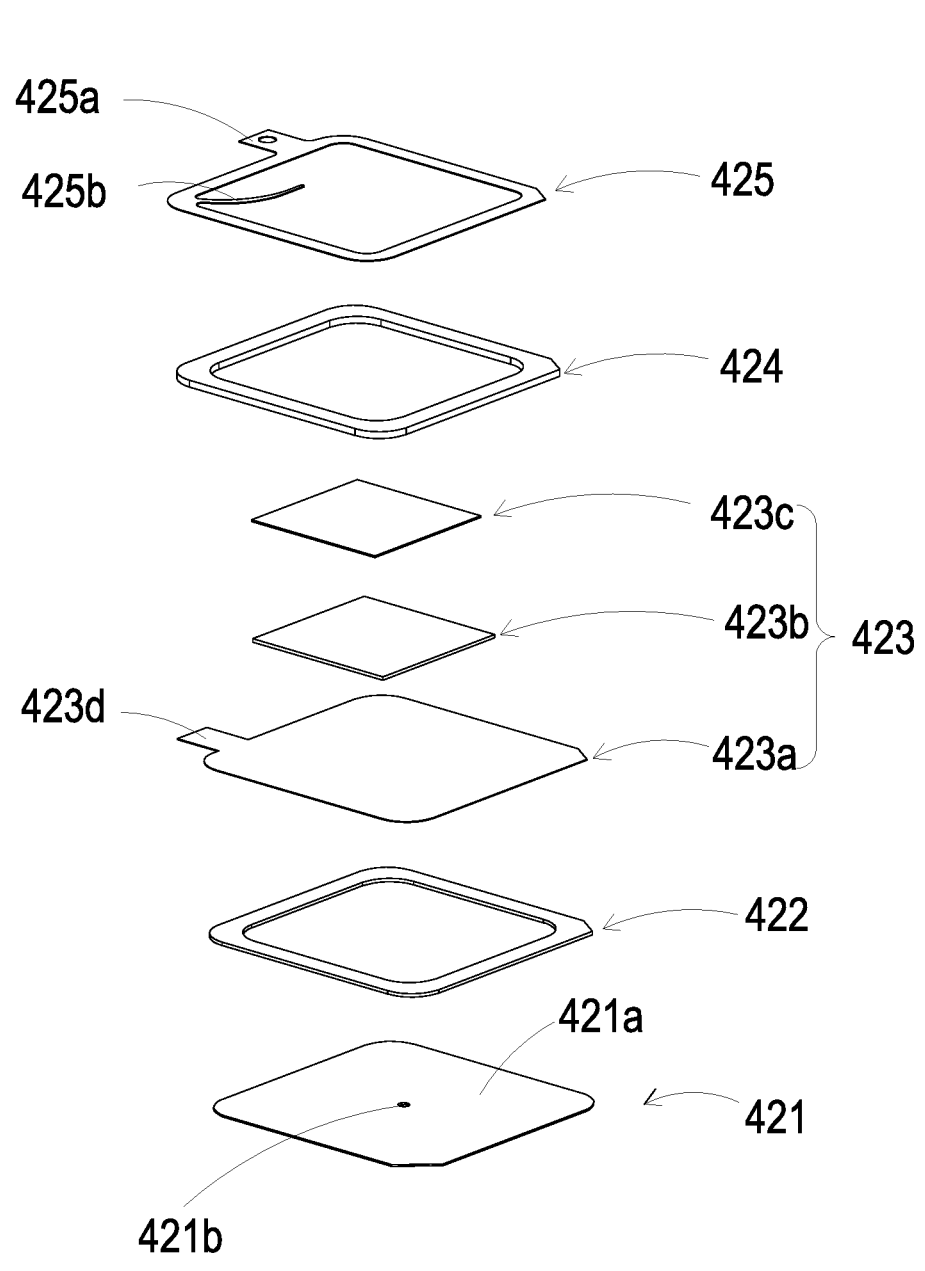
FIG. 9A is a schematic exploded view illustrating the piezoelectric actuator of the gas detection main part of the present disclosure.
Figure 9B:
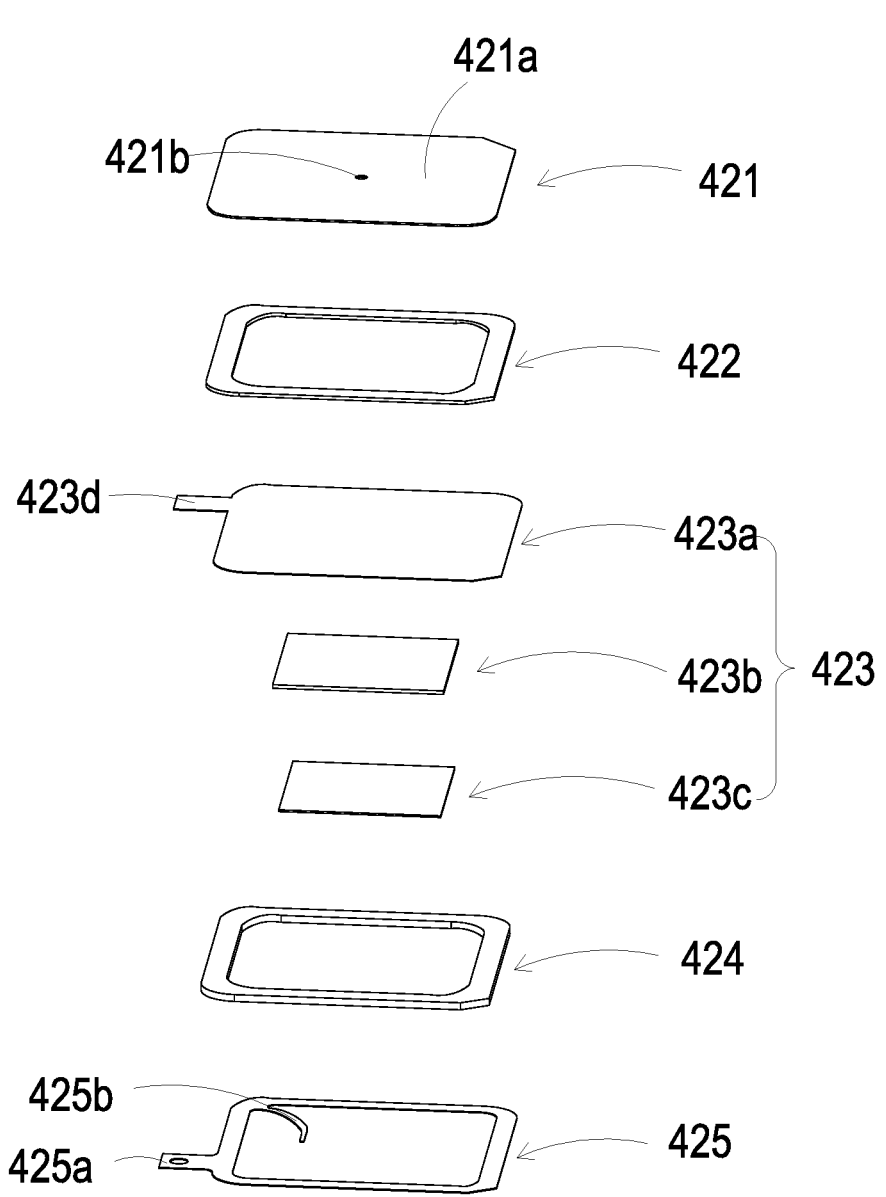
FIG. 9B is a schematic exploded view illustrating the piezoelectric actuator of the gas detection main part of the present disclosure from another perspective angle.

Please refer to FIGS. 9A and 9B. In the embodiment, the piezoelectric actuating element 42 includes a gas-injection plate 421, a chamber frame 422, an actuator element 423, an insulation frame 424 and a conducting frame 425. The gas-injection plate 421 is made by a flexible material and includes a suspension plate 421a and a hollow aperture 421b. The suspension plate 421a is a sheet structure permitted to undergo a bending deformation. Preferably but not exclusively, the shape and size of the suspension plate 421a are accommodated to an inner edge of the gas-guidingcomponent loading region 415, but not limited thereto. The shape of the suspension plate 421a is selected from the group consisting of a square, a circle, an ellipse, a triangle and a polygon. The hollow aperture 421b passes through a center of the suspension plate 421a for allowing the gas to flow therethrough.

Figure 10A:
FIG. 10A is a schematic cross-section view illustrating the piezoelectric actuator of the gas detection main part assembled in the gas-guiding-component loading region of the present disclosure.

Please refer to FIG. 9A, FIG. 9B and FIG. 10A. In the embodiment, the chamber frame 422 is carried and stacked on the gas-injection plate 421, and the shape of the chamber frame 422 is corresponding to that of the gas-injection plate 421. The actuator element 423 is carried and stacked on the chamber frame 422. A resonance chamber 426 is collaboratively defined by the actuator element 423, the chamber frame 422 and the suspension plate 421a, and is formed between the actuator element 423, the chamber frame 422 and the suspension plate 421a. The insulation frame 424 is carried and stacked on the actuator element 423, and the appearance of the insulation frame 424 is similar to that of the chamber frame 422. The conducting frame 425 is carried and stacked on the insulation frame 424, and the appearance of the conducting frame 425 is similar to that of the insulation frame 424. Moreover, the conducting frame 425 includes a conducting pin 425a and a conducting electrode 425b. The conducting pin 425a is extended outwardly from an outer edge of the conducting frame 425, and the conducting electrode 425b is extended inwardly from an inner edge of the conducting frame 425. In addition, the actuator element 423 further includes a piezoelectric carrying plate 423a, an adjusting resonance plate 423b and a piezoelectric plate 423c. The piezoelectric carrying plate 423a is carried and stacked on the chamber frame 422. The adjusting resonance plate 423b is carried and stacked on the piezoelectric carrying plate 423a. The piezoelectric plate 423c is carried and stacked on the adjusting resonance plate 423b. The adjusting resonance plate 423b and the piezoelectric plate 423c are accommodated in the insulation frame 424. The conducting electrode 425b of the conducting frame 425 is electrically connected to the piezoelectric plate 423c. In the embodiment, the piezoelectric carrying plate 423a and the adjusting resonance plate 423b are made by a conductive material. The piezoelectric carrying plate 423a includes a piezoelectric pin 423d. The piezoelectric pin 423d and the conducting pin 425a are electrically connected to a driving circuit (not shown) of the driving circuit board 43, so as to receive a driving signal, such as a driving frequency and a driving voltage. Through this structure, a circuit is formed by the piezoelectric pin 423d, the piezoelectric carrying plate 423a, the adjusting resonance plate 423b, the piezoelectric plate 423c, the conducting electrode 425b, the conducting frame 425 and the conducting pin 425a for transmitting the driving signal. Moreover, the insulation frame 424 is insulated between the conducting frame 425 and the actuator element 423, so as to avoid the occurrence of short circuit. Thereby, the driving signal can be transmitted to the piezoelectric plate 423c. After receiving the driving signal such as the driving frequency and the driving voltage, the piezoelectric plate 423c deforms due to the piezoelectric effect, and the piezoelectric carrying plate 423a and the adjusting resonance plate 423b are driven to generate the bending deformation in the reciprocating manner.

As described above, the adjusting resonance plate 423b is located between the piezoelectric plate 423c and the piezoelectric carrying plate 423a and is served as a cushion between the piezoelectric plate 423c and the piezoelectric carrying plate 423a. Thereby, the vibration frequency of the piezoelectric carrying plate 423a is adjustable. Basically, the thickness of the adjusting resonance plate 423b is greater than the thickness of the piezoelectric carrying plate 423a. Since the thickness of the adjusting resonance plate 423b is adjustable, the vibration frequency of the actuator element 423 can be adjusted accordingly.

Please refer to FIG. 9A, FIG. 9B and FIG. 10A. In the embodiment, the gas-injection plate 421, the chamber frame 422, the actuator element 423, the insulation frame 424 and the conducting frame 425 are stacked and positioned in the gas-guiding-component loading region 415 sequentially so that the piezoelectric actuating element 42 is supported and positioned in the gas-guiding-component loading region 415. The bottom of the gas-injection plate 421 is fixed on the positioning protrusions 415b for supporting and positioning so that a vacant space 421c in the piezoelectric actuating element 42 is defined between the suspension plate 421a and an inner edge of the gas-guiding-component loading region 415 for gas flowing.

Please refer to FIG. 10A. A flowing chamber 427 is formed between the gas-injection plate 421 and the bottom surface of the gas-guiding-component loading region 415. The flowing chamber 427 is in fluid communication with the resonance chamber 426 between the actuator element 423, the chamber frame 422 and the suspension plate 421a through the hollow aperture 421b of the gas-injection plate 421. Through controlling the vibration frequency of the gas in the resonance chamber 426 to be close to the vibration frequency of the suspension plate 421a, the Helmholtz resonance effect is generated between the resonance chamber 426 and the suspension plate 421a, so as to improve the efficiency of gas transportation.

Figure 10B:
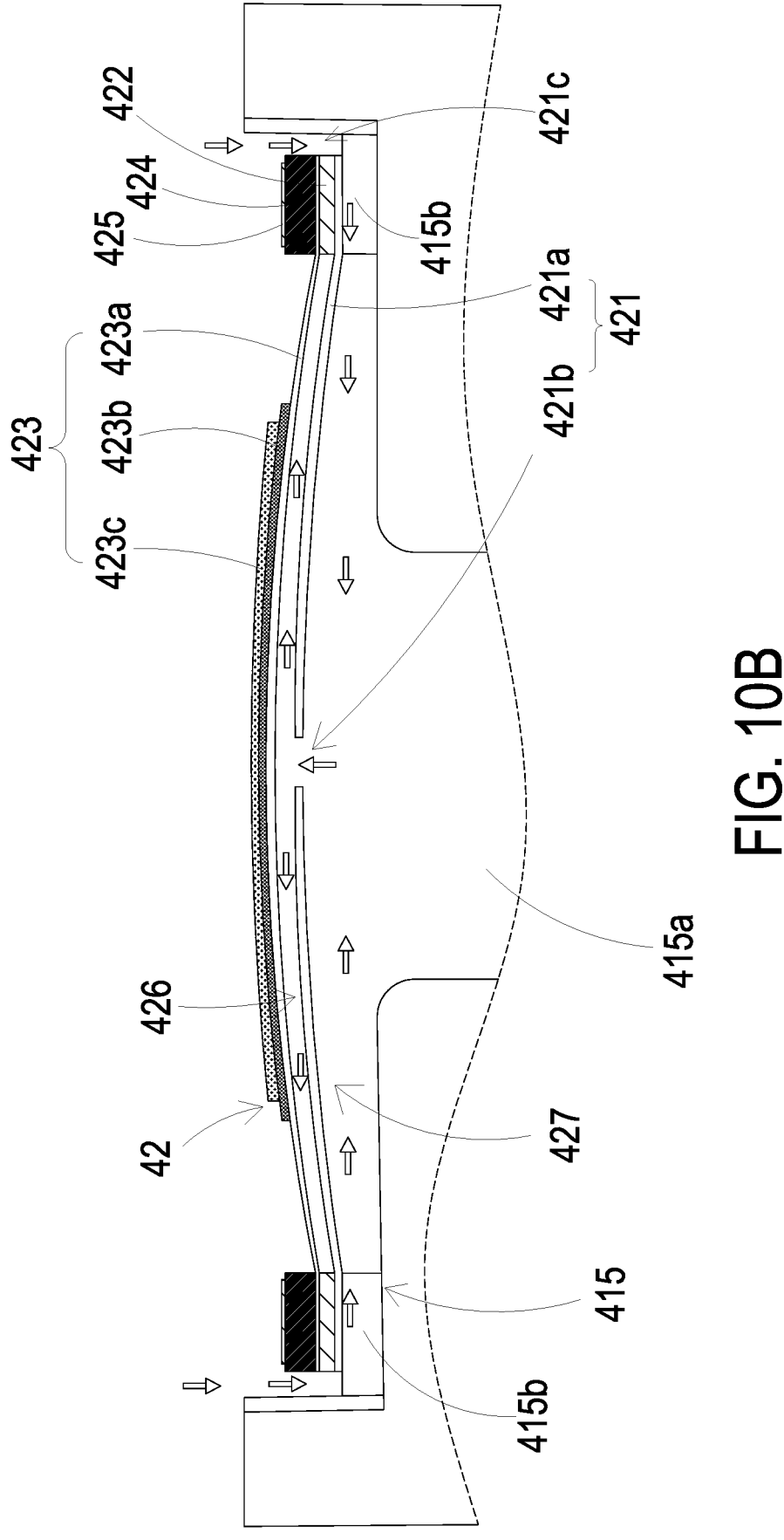
FIGS. 10B and 10C schematically illustrate the operation steps of the piezoelectric actuator of FIG. 10A.
Figure 10C:
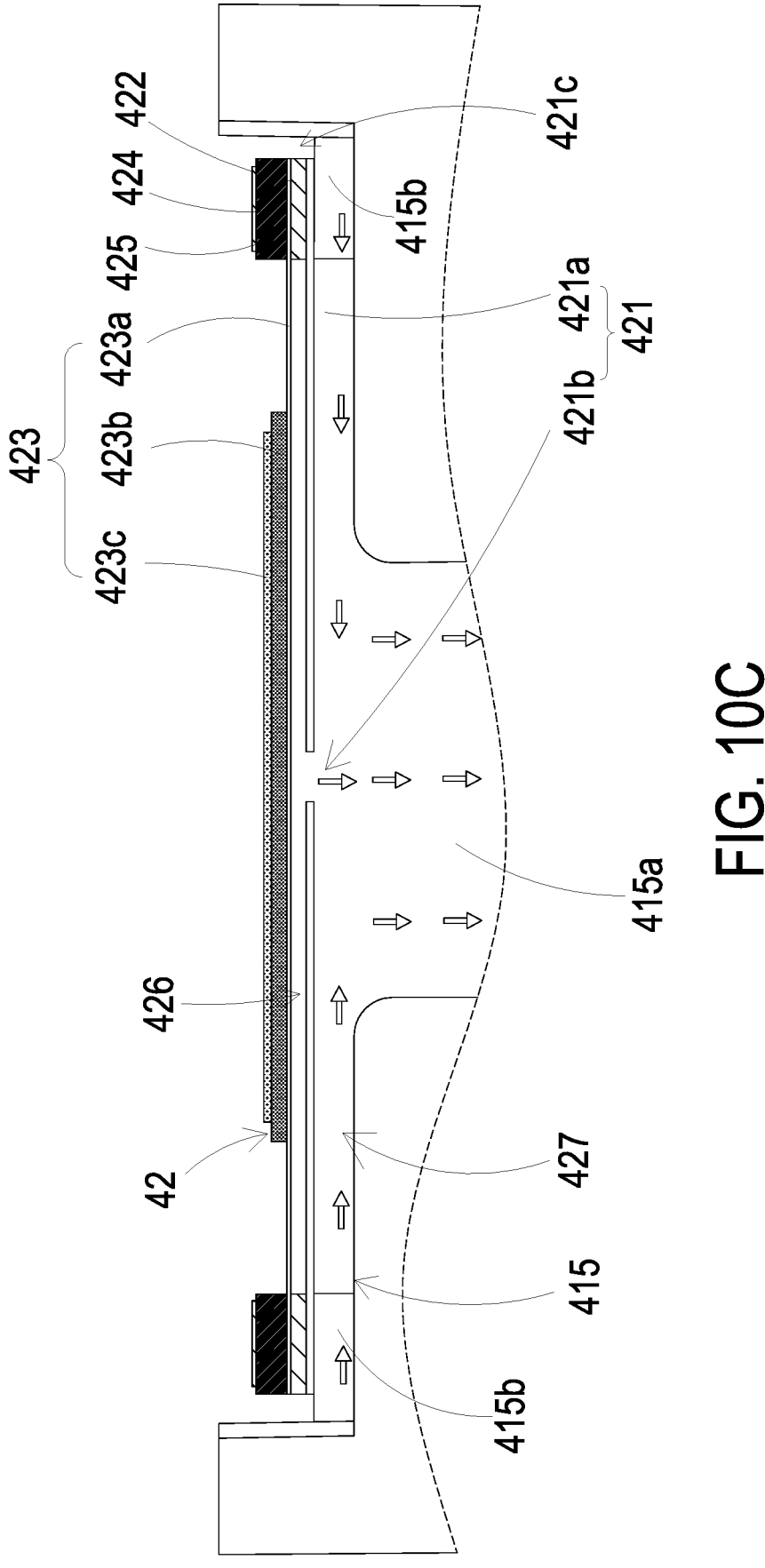

Please refer to FIG. 10B. When the piezoelectric plate 423c is moved in a direction away from the bottom surface of the gas-guiding-component loading region 415, the piezoelectric plate 423c drives the suspension plate 421a of the gas-injection plate 421 to move in a direction away from the bottom surface of the gas-guiding-component loading region 415. In that, the volume of the flowing chamber 427 expands rapidly, and the internal pressure of the flowing chamber 427 decreases to form a negative pressure. Accordingly, the gas outside the piezoelectric actuating element 42 is inhaled through the vacant space 421c and enters the resonance chamber 426 through the hollow aperture 421b. Consequently, the pressure in the resonance chamber 426 is increased to generate a pressure gradient. Further, as shown in FIG. 10C, when the piezoelectric plate 423c drives the suspension plate 421a of the gas-injection plate 421 to move toward the bottom surface of the gas-guiding-component loading region 415, the gas in the resonance chamber 426 is discharged out rapidly through the hollow aperture 421b, and the gas in the flowing chamber 427 is compressed, thereby the converged gas is quickly and massively ejected out of the flowing chamber 427 under the condition close to an ideal gas state of the Benulli's law, and transported to the ventilation hole 415a of the gas-guiding-component loading region 415. By repeating the above operation steps shown in FIG. 10B and FIG. 10C, the piezoelectric plate 423c is driven to generate the bending deformation in a reciprocating manner. According to the principle of inertia, since the gas pressure inside the resonance chamber 426 is lower than the equilibrium gas pressure after the converged gas is ejected out, the gas is introduced into the resonance chamber 426 again. Moreover, the vibration frequency of the gas in the resonance chamber 426 is controlled to be close to the vibration frequency of the piezoelectric plate 423c, so as to generate the Helmholtz resonance effect to achieve the gas transportation at high speed and in large quantities.

In addition, as shown in FIG. 11A, the gas is inhaled through the inlet opening 461*a* of the outer cover 46, flows into the gas-inlet groove 414 of the base 41 through the gas-inlet 414*a*, and is transported to the position of the particulate sensor 45. Further, as shown in FIG. 11B, the piezoelectric actuating element 42 is enabled continuously to inhale the gas into the gas-inlet path, and facilitate the gas to be introduced rapidly and stably and transported through the space above the particulate sensor 45. Meanwhile, a light beam emitted by the laser component 44 passes through the transparent window 414*b* to irritate on the suspended particles contained in the gas flowing through the space above the particulate sensor 45 in the gas-inlet groove 414. When the light beam irradiates on the suspended particles contained in the gas, the light beam scatters and generates projected light spots accordingly. The projected light spots are received and calculated by the particulate sensor 45 for obtaining related information about the size and concentration of the suspended particles contained in the gas. Moreover, the gas above the particulate sensor 45 is continuously driven and transported by the piezoelectric actuating element 42 to flow into the ventilation hole 415*a* of the gas-guiding-component loading region 415, and transport to the first section 416*b* of the gas-outlet groove 416. As shown in FIG. 11C, after the gas flows into the first section 416*b* of the gas-outlet groove 416, the gas is continuously transported into the first section 416*b* by the piezoelectric actuating element 42, and the gas in the first section 416*b* is pushed to the second section 416*c*. Finally, the gas is discharged out through the gas-outlet 416*a* and the outlet opening 461*b*.

Figure 12:
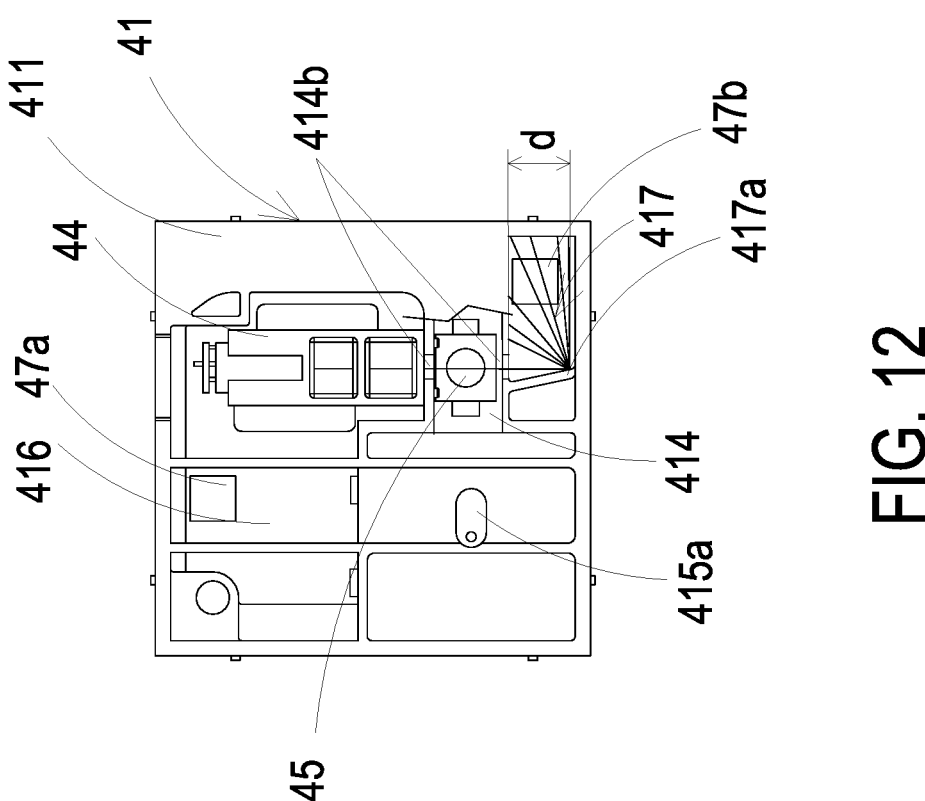
FIG. 12 schematically illustrates a path of a light beam emitted by the laser component of the gas detection main part of the present disclosure.
Figure 13:
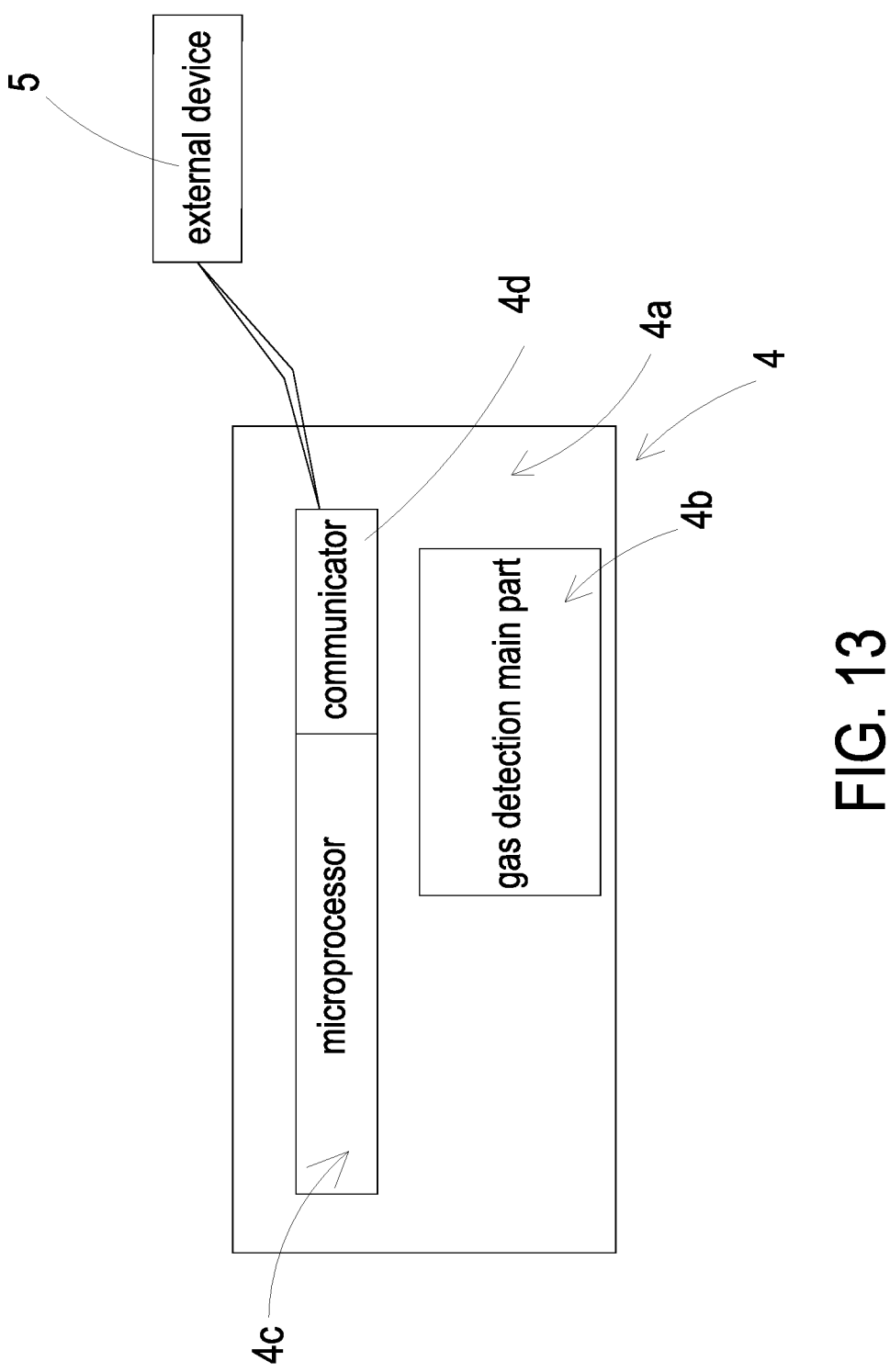
FIG. 13 is a block diagram illustrating a configuration of a controlling circuit board and the related components of the purification device of exercise environment of the present disclosure.

As shown in FIG. 12, the base 41 further includes a light trapping region 417. The light trapping region 417 is hollowed out from the first surface 411 to the second surface 412 and is spatially corresponding to the laser loading region 413. In the embodiment, the light beam emitted by the laser component 44 is projected into the light trapping region 417 through the transparent window 414*b*. The light trapping region 417 includes a light trapping structure 417*a* having an oblique cone surface. The light trapping structure 417*a* is spatially corresponding to the path of the light beam emitted by the laser component 44. In addition, the light beam emitted by the laser component 44 is reflected into the light trapping region 417 by the oblique cone surface of the light trapping structure 417*a*, so as to prevent the light beam from reflecting back to the position of the particulate sensor 45. In the embodiment, a light trapping distance d is maintained between the transparent window 414*b* and a position where the light trapping structure 417*a* receives the light beam. Accordingly, the light beam projected on the light trapping structure 417*a* is avoid reflecting back to the position of the particulate sensor 45 directly due to excessive stray light generated after reflection, which causes a distortion of detection accuracy.

Please refer to FIG. 5C and FIG. 12. The gas detection module 4 of the present disclosure not only detects the suspended particles contained in the gas but also further detects the characteristics of the introduced gas. Preferably but not exclusively, the gas can be detected is selected from the group consisting of formaldehyde, ammonia, carbon monoxide, carbon dioxide, oxygen, ozone and a combination thereof. In the embodiment, the gas detection module 4 further includes a first volatile-organic-compound sensor 47*a*. The first volatile-organic-compound sensor 47*a* positioned and disposed on the driving circuit board 43 is electrically connected to the driving circuit board 43, and accommodated in the gas-outlet groove 416, so as to detect the gas flowing through the gas-outlet path. Thus, the concentration or the characteristics of volatile organic compounds contained in the gas in the gas-outlet path can be detected. Alternatively, in an embodiment, the gas detection module 4 further includes a second volatile-organic-compound sensor 47*b*. The second volatile-organic-compound sensor 47*b* positioned and disposed on the driving circuit board 43 is electrically connected to the driving circuit board 43 and is accommodated in the light trapping region 417. Thus, the concentration or the characteristics of volatile organic compounds contained in the gas, which flows through the gas-inlet path of the gas-inlet groove 414 and transports into the light trapping region 417 through the transparent window 414*b*, can be detected by the second volatile-organic-compound sensor 47*b*.

In summary, the present disclosure provides a purification device of exercise environment. A gas detection module is utilized to monitor the air quality of the exercise environment around the exerciser at any time, and a purification unit is utilized to provide a solution for purifying and improving the air quality. By the combination of the gas detection module, the purification unit and the gas guider, the exerciser is prevented from breathing harmful gas in the indoor and/or outdoor exercise environment. Moreover, the exerciser can also receive an real-time information for warning notice, so as to alarm and notify the exerciser in the exercise environment to take preventive measures immediately and away from the harmful exercise environment.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A purification device of exercise environment, comprising:

a main body having at least one gas inlet and at least one gas outlet; and a purification unit, a gas guider and a gas detection module disposed in the main body, wherein the gas detection module comprises a gas detection main part, the gas detection main part comprises a base, a piezoelectric actuator, a driving circuit board, a laser component, a particle sensor and an outer cover, wherein the base comprising:

a first surface;

a second surface opposite to the first surface;

a gas-guiding-component loading region concavely formed from the second surface;

the piezoelectric actuator accommodated in the gas-guiding-component loading region;

the driving circuit board covering and attached to the second surface of the base;

a laser component positioned and disposed on the driving circuit board, electrically connected to the driving circuit board, and accommodated in the laser loading region;

the particle sensor positioned and disposed on the driving circuit board, electrically connected to the driving circuit board, and disposed at an orthogonal position and an outer cover covering the first surface of the base and comprising a side plate, wherein a gas in an exercise environment is introduced through the at least one gas inlet and filtered by the purification unit, the gas in the exercise environment is continuously transported by the gas guider, passed through the at least one gas inlet, flowed through the purification unit, and provided to a breathing region around a nose of an exerciser, wherein the gas detection module detects a gas information and a particulate cleanliness of the air in the exercise environment, and the particulate cleanliness of the gas in the breathing region of the exerciser reaches 0~20 µg/m³ accordingly.

2. The purification device of exercise environment according to claim 1, wherein the main body has a directional guiding element disposed on the at least one gas outlet of the main body, a filtered gas amount of over 60 L/min is discharged out through the at least one gas outlet by the gas guider to form a directional filtered gas flow, the directional filtered gas flow is provided to the breathing region around the nose of the exerciser, and the particulate cleanliness of the gas in the breathing region reaches 0~20 µg/m³.

3. The purification device of exercise environment according to claim 1, wherein a filtered gas flow with a clean air delivery rate of over 500 m³/hr is discharged out through the at least one gas outlet by the gas guider, and the filtered gas flow is provided to the breathing region around the nose of the exerciser so that the particulate cleanliness of the gas in the breathing region reaches 0~20 µg/m³.

4. The purification device of exercise environment according to claim 1, wherein the main body further includes a gas-flow channel disposed between the gas inlet and the gas outlet, the purification unit is disposed in the gas-flow channel for filtering the gas, and the gas guider is disposed in the gas-flow channel and is located at a side of the purification unit to guide the gas inhaled through the gas inlet to flow through the purification unit for filtering and purifying and discharge out through the gas outlet.

5. The purification device of exercise environment according to claim 4, wherein the gas detection module is disposed in the gas-flow channel and comprises a controlling circuit board, a microprocessor and a communicator, the gas detection module detects the gas introduced from the exercise environment outside the main body to obtain the gas information and the particulate cleanliness for calculating and processing, and the gas detection module controls the enablement and disablement of the gas guider accordingly, wherein when the gas guider is operated in the enable state, the gas is inhaled through the gas inlet, flows through the purification unit for filtering and purifying, and is discharged out through the gas outlet, so as to provide the exerciser with a purified gas.

6. The purification device of exercise environment according to claim 1, wherein the purification unit is an HEPA filter screen.

7. The purification device of exercise environment according to claim 6, wherein the HEPA filter screen is coated with a layer of chloride-dioxide clean factor to inhibit viruses and bacteria in the gas.

8. The purification device of exercise environment according to claim 6, wherein the HEPA filter screen is coated with an herbal protective layer extracted from ginkgo and Japanese *Rhus chinensis* to form an herbal protective anti-allergic filter, so as to resist allergy and destroy a surface protein of influenza virus in the gas passing through the HEPA filter screen.

9. The purification device of exercise environment according to claim 6, wherein the HEPA filter screen is coated with a silver ion to inhibit viruses and bacteria in the gas.

10. The purification device of exercise environment according to claim 6, wherein the purification unit comprises a photo-catalyst unit combined with the HEPA filter screen, the photo-catalyst unit comprises a photo-catalyst and an ultraviolet lamp, and the photo-catalyst is irradiated by the ultraviolet lamp to decompose the gas for filtering and purifying.

11. The purification device of exercise environment according to claim 6, wherein the purification unit comprises a photo-plasma unit combined with the HEPA filter screen, the photo-plasma unit comprises a nanometer irradiation tube, and the nanometer irradiation tube irradiates the gas to decompose volatile organic compounds contained in the gas, thereby purifying the gas.

12. The purification device of exercise environment according to claim 6, wherein the purification unit comprises a negative ionizer combined with the HEPA filter screen, the negative ionizer comprises at least one electrode wire, at least one dust collecting plate and a boost power supply, and when a high voltage is discharged through the electrode wire, particles contained in the gas are adsorbed by the dust collecting plate, thereby filtering and purifying the gas.

13. The purification device of exercise environment according to claim 6, wherein the purification unit comprises a plasma ion unit combined with the HEPA filter screen, the plasma ion unit comprises a first electric-field protection screen, an adsorption filter screen, a high-voltage discharge electrode, a second electric-field protection screen and a boost power supply device, the boost power supply device provides the high-voltage discharge electrode with a high voltage to discharge so as to generate a high-voltage plasma column, and viruses and bacteria contained in the gas are decomposed by plasma ion of the high-voltage plasma column.

14. The purification device of exercise environment according to claim 1, wherein the gas guider is an actuating pump, the actuating pump comprises:

a gas inlet plate having at least one gas inlet aperture, at least one convergence channel and a convergence chamber, wherein the at least one gas inlet aperture is disposed to inhale the gas, the at least one gas inlet aperture correspondingly penetrates through the gas inlet plate into the at least one convergence channel, and the at least one convergence channel is converged to the convergence chamber so that the gas inhaled through the at least one gas inlet aperture is converged into the convergence chamber;

a resonance plate assembled on the gas inlet plate and having a central aperture, a movable part and a fixed part, wherein the central aperture is located at a center of the resonance plate and is corresponding in position to the convergence chamber of the gas inlet plate, the movable part surrounds the central aperture and is corresponding in position to the convergence chamber, and the fixed part is disposed around a periphery of the resonance plate and is firmly attached on the gas inlet plate; and a piezoelectric actuator assembled on the resonance plate and corresponding in position to the resonance plate, wherein a chamber space is formed between the resonance plate and the piezoelectric actuator, when the piezoelectric actuator is driven, the gas is introduced through the at least one gas inlet aperture of the gas inlet plate, converged to the convergence chamber through the at least one convergence channel, and flowed through the central aperture of the resonance plate, and the movable part of the resonance plate and the piezoelectric actuator are resonated to transport the gas, wherein the actuating pump further comprises a first insulation plate, a conducting plate and a second insulation plate, and the gas inlet plate, the resonance plate, the piezoelectric actuator, the first insulation plate, the conducting plate and the second insulation plate are stacked and assembled sequentially.

15. The purification device of exercise environment according to claim 14, wherein the piezoelectric actuator of the actuating pump comprises:

a suspension plate which is square-shaped and is permitted to undergo a bending deformation;

an outer frame disposed around a periphery of the suspension plate;

at least one bracket connected between the suspension plate and the outer frame for elastically supporting the suspension plate; and a piezoelectric element having a side, wherein a length of the side is less than or equal to a length of a side of the suspension plate, and the piezoelectric element is attached to a surface of the suspension plate, wherein when a voltage is applied to the piezoelectric element, the suspension plate is driven to undergo the bending deformation.

16. The purification device of exercise environment according to claim 14, wherein the piezoelectric actuator of the actuating pump comprises:

a suspension plate which is square-shaped and is permitted to undergo a bending deformation;

an outer frame disposed around a periphery of the suspension plate;

at least one bracket connected between the suspension plate and the outer frame for elastically supporting the suspension plate, wherein a surface of the suspension plate and a surface of the outer frame are non-coplanar, and the chamber space is maintained between a surface of the suspension plate and the resonance plate; and a piezoelectric element having a side, wherein a length of the side is less than or equal to a length of a side of the suspension plate, and the piezoelectric element is attached to a surface of the suspension late, wherein when a voltage is applied to the piezoelectric element, the suspension plate is driven to undergo the bending deformation.

17. The purification device of exercise environment according to claim 5, wherein the gas detection main part, the microprocessor, the communicator and a power unit are integrally packaged on the controlling circuit board and are electrically connected to the controlling circuit board, the gas detection main part detects the gas introduced from an outside of the main body to acquire the gas information, the microprocessor receives the gas information and the particulate cleanliness for calculating and processing, the communicator transmits the gas information and the particulate cleanliness received from the microprocessor to an external device, the external device provides a notification or an alarm, and the external device is a mobile, a clouding processing device or a computer system.

18. The purification device of exercise environment according to claim 1, wherein the base comprising:

a laser loading region hollowed out from the first surface to the second surface;

a gas-inlet groove concavely formed on the second surface and disposed neighboring to the laser loading region, wherein the gas-inlet groove comprises a gas-inlet and two side walls, and a transparent window is opened on the two lateral walls and is in communication with the laser loading region;

penetrated a bottom surface of the gas-guiding-component loading region, wherein the gas-guiding-component loading region has four positioning protrusions disposed at four corners thereof; and a gas-outlet groove including a first section and a second section, wherein the first section is concavely formed from the first surface on a region spatially corresponding to a bottom surface of the gas-guiding-component loading region, the second section is hollowed out from the first surface to the second surface in a region where the first surface is not aligned with the gas-guiding-component loading region, the gas-outlet groove is in fluid communication with the ventilation hole, and a gas-outlet is disposed in the gas-outlet groove;

the laser component is-accommodated in the laser loading region, wherein a path of a light beam emitted by the laser component passes through the transparent window and extends in a direction perpendicular to the gas-inlet groove;

the particulate sensor accommodated at a position where the gas-inlet groove and the path of the light beam emitted by the laser component are orthogonal intersection, wherein suspended particles in the air passing through the gas-inlet groove and irradiated by the light beam emitted by the laser component are detected by the particulate sensor; and the outer cover having a side plate, wherein the side plate has an inlet opening spatially corresponding to the gas-inlet of the base and an outlet opening spatially corresponding to the gas-outlet of the base, wherein the first surface of the base is covered with the outer cover and the second surface of the base is covered with the driving circuit board, so as to define a gas-inlet path and a gas-outlet path by the gas-inlet groove and the gas-outlet groove respectively, the piezoelectric actuating element accelerates the progress of guiding the gas inhaled outside the base into the gas-inlet path through the inlet opening and to pass through the particulate sensor for detecting a concentration of the suspended particles contained in the gas, wherein the gas is transported out of the gas-outlet path through the ventilation hole and then discharged out through the outlet opening by the piezoelectric actuating element.

19. The purification device of exercise environment according to claim 18, wherein the piezoelectric actuating element comprises:

a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element carried and stacked on the chamber frame, wherein a voltage is applied on the actuator element, the actuator element generates a bending deformation in a reciprocating manner;

an insulation frame carried and stacked on the actuator element; and a conducting frame carried and stacked on the insulation frame, wherein the gas-injection plate is fixed on the four positioning protrusions in the gas-guiding-component loading region for supporting and positioning so that the gas-injection plate and an inner edge of the gas-guiding-component loading region define a vacant space surrounding the gas-injection plate for gas to flow therethrough, a flowing chamber is formed between the gas-injection plate and a bottom surface of the gas-guiding-component loading region, and a resonance chamber is formed between the actuator element, the chamber frame and the suspension plate, wherein when the actuator element is enabled to drive the gas-injection plate to move in resonance therewith, the suspension plate of the gas-injection plate is driven to generate a bending deformation in a reciprocating manner, and the gas is inhaled into the flowing chamber through the vacant space and discharged out through the bending deformation of the suspension plate, thereby achieving gas transportation;

wherein the actuator element comprises:

a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to generate a bending deformation in a reciprocating manner by applying an voltage.

20. The purification device of exercise environment according to claim 19, further comprising a first volatile-organic-compound sensor positioned and disposed on the driving circuit board, electrically connected to the driving circuit board, and accommodated in the gas-outlet groove, so as to detect the gas flowing through the gas-outlet path.

\* \* \* \* \*